United States Patent [19]
Mandecki

[11] Patent Number: 6,051,377
[45] Date of Patent: *Apr. 18, 2000

[54] MULTIPLEX ASSAY FOR NUCLEIC ACIDS EMPLOYING TRANSPONDERS

[75] Inventor: Wlodek Mandecki, Libertyville, Ill.

[73] Assignee: Pharmaseq, Inc., Monmouth Junction, N.J.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/762,812

[22] Filed: Dec. 9, 1996

Related U.S. Application Data

[63] Continuation-in-part of application No. 08/564,851, Nov. 30, 1995, abandoned.

[51] Int. Cl.⁷ .............................. C12Q 1/68; C12P 19/34
[52] U.S. Cl. .............................................. 435/6; 435/91.2
[58] Field of Search ........................................ 435/6, 91.2

[56] References Cited

U.S. PATENT DOCUMENTS

| | | |
|---|---|---|
| 4,177,253 | 12/1979 | Davies . |
| 4,297,337 | 10/1981 | Mansfield et al. . |
| 4,452,773 | 6/1984 | Molday . |
| 4,454,234 | 6/1984 | Czerlinski . |
| 4,556,883 | 12/1985 | Strietzel . |
| 4,672,040 | 6/1987 | Josephson . |
| 4,777,145 | 10/1988 | Luotola et al. . |
| 4,778,769 | 10/1988 | Forrest et al. . |
| 4,822,566 | 4/1989 | Newman . |
| 4,857,893 | 8/1989 | Carroll . |
| 4,923,819 | 5/1990 | Fernandez et al. . |
| 4,941,201 | 7/1990 | Davis . |
| 4,965,188 | 10/1990 | Mullis et al. . |
| 5,019,815 | 5/1991 | Lemelson . |
| 5,034,192 | 7/1991 | Wrighton et al. . |
| 5,071,774 | 12/1991 | Vorpahl et al. . |
| 5,153,583 | 10/1992 | Murdoch . |
| 5,200,051 | 4/1993 | Cozzette et al. . |
| 5,202,231 | 4/1993 | Drmanac et al. . |
| 5,214,409 | 5/1993 | Beigel . |
| 5,218,343 | 6/1993 | Stobbe et al. . |
| 5,223,851 | 6/1993 | Hadden et al. . |
| 5,235,326 | 8/1993 | Beigel et al. . |
| 5,245,332 | 9/1993 | Katzenstein . |
| 5,250,944 | 10/1993 | Urbas et al. . |
| 5,252,962 | 10/1993 | Urbas et al. . |
| 5,257,011 | 10/1993 | Biegel . |
| 5,262,772 | 11/1993 | Urbas et al. . |
| 5,266,926 | 11/1993 | Mroczkowski et al. . |
| 5,347,263 | 9/1994 | Carroll et al. . |
| 5,422,636 | 6/1995 | Urbas et al. . |
| 5,440,300 | 8/1995 | Spillman, Jr. . |
| 5,445,970 | 8/1995 | Rohr . |
| 5,466,348 | 11/1995 | Holm-Kennedy . |
| 5,481,262 | 1/1996 | Urbas et al. . |
| 5,491,097 | 2/1996 | Ribi et al. . |
| 5,492,806 | 2/1996 | Drmanac et al. . |
| 5,525,464 | 6/1996 | Drmanac et al. . |
| 5,552,270 | 9/1996 | Khrapko et al. . |
| 5,641,634 | 6/1997 | Mandecki .................................... 435/6 |
| 5,736,332 | 4/1998 | Mandecki . |

FOREIGN PATENT DOCUMENTS

| | | |
|---|---|---|
| 0526173 A2 | 2/1993 | European Pat. Off. . |
| WO90/13666 | 11/1990 | WIPO . |
| WO93/04199 | 3/1993 | WIPO . |
| WO93/21340 | 10/1993 | WIPO . |
| WO96/36436 | 11/1996 | WIPO . |
| WO97/19958 | 6/1997 | WIPO . |
| WO97/20073 | 6/1997 | WIPO . |
| WO97/20074 | 6/1997 | WIPO . |

OTHER PUBLICATIONS

Service, Science 270:577, 1995.
Hu Hman et al, Nucleic Acid Res 17:4937–4946, 1989.
Albretsen, C et al. "Applications of magnetic beads with covalently attached oligonucleotides in hybridization: Isolation and detection of specific measles virus mRNA from a crude cell lysate" *Analytical Biochemistry* (1990) vol. 189, pp. 40–50.
Alper, J. "Drug Discovery on the assembly line" *Science* (Jun. 3, 1994) vol. 264, pp. 1399–1401.
Atkinson, T et al. "A convenient procedure for the synthesis of oligodeoxyribonucleotide affinity columns for the isolation of mRNA" *Nucleic Acids Research*, (1988), vol. 16, No. 13.
Cargill, JF and BE Toyonaga. *The Chemical Factory: An Assembly Line Approach to Automated Combinatorial Chemistry on Solid Phase.*
Caruthers, MH et al. "Deoxyoligonucleotide synthesis via the phosphoramidite method" *Gene Amplification and Analysis*, vol. III, (TS Papas et al., eds.) Elsevier Press, Amsterdam.
Drmanac, R et al. "DNA sequence determination by hybridization: a strategy for efficient large–scale sequencing." *Science* (1993) vol. 260, pp. 1649–1652.
Flore, F et al. "The Abbott IMx Automated Benchtop Immunochemistry Analyzer System" *Clinical Chemistry* (1998) vol. 34, No. 9.
Ghosh, SS and GF Musso. "Covalent attachment of oligonucleotides to solid supports" *Nucleic Acids Research*, (1987) vol. 15, No. 13.

(List continued on next page.)

*Primary Examiner*—Eggerton A. Campbell
*Attorney, Agent, or Firm*—Brinks Hofer Gilson & Lione

[57] ABSTRACT

Disclosed are materials and methods for performing multiplex assays for nucleic acids, in which a transponder is associated with the bead(s) forming the solid phase used in the assay, nucleic acid probes are bound to the surface of the particles, and data concerning the assay is encoded on the transponder. A dedicated read/write device is used to remotely encode or read the data.

19 Claims, 14 Drawing Sheets

OTHER PUBLICATIONS

Gingeras TR et al. "Hybridization properties of immobilized nucleic acids" *Nucleic Acids Research* (1987) vol. 15, No. 13.

Hooft van Hujisduijnen, RAM et al. "A means to reduce the complexity of oligonucleotides encoding degenerated peptides" *Nucleic Acids Research* (1992) vol. 20, No. 4.

Hultman et al. "Direct solid phase sequencing of genomic DNA using magnetic beads as solid support" *Nucleic Acids Research* (1989) vol. 17, No. 13, pp. 4937–4946.

Ihalainen et al. *Biotechniques* (1994) vol. 16, pp. 938–943.

Kurstak, E. *Enyzme Immunodiagnostics* (1986) pp. 13–22, Academic Press, NY.

Lam, KS et al. "A new type of synthetic peptide library for identifying ligand–binding activity" *Nature* (Nov. 7, 1991) vol. 354, pp. 82–84.

Maskos, E. et al. "Oligonucleotide hybridisations [sic] on glass supports: a novel linker for oligonucleotide synthesis and hybridisation [sic] properties of oligonucleotides synthesized in situ" *Nucleic Acids Research* (1992) vol. 20, No. 7, pp. 1679–1684.

McHugh, T. "Flow Microsphere Immunoassay for the Quantitative and Simultaneous Detection of Multiple Soluble Analytes" *Methods in Cell Biology* (1990) vol. 42, pp. 575–595.

Mirzabekov, AD. "DNA sequencing by hybridization—a megasequencing method and a diagnostic tool" *Tibtech* (1994) vol. 12.

Moran et al. "Radio frequency tag encoded combinatorial library method for the discovery of tripeptide–substituted cinnamic acid inhibitors of the protein tyrosine phosphatase PTP1B" *J. Am. Chem Soc.* (1995) vol. 117, pp. 10787–10788.

Morrissey, NE et al. "Modified method for determining carcinoembryonic antigen in the presence of human anti–murine antibodies" *Clinical Chemistry* (1993) vol. 39, No. 3.

Nicolaou et al. "Radiofrequency encoded combinatorial chemistry" *Angew. Chem Int. Ed.* (1995), vol. 34, No. 2I0, pp. 2289–2291.

Pease, AC et al. "Light–generated oligonucleotide arrays for rapid DNA sequence analysis" *Proc. Natl. Acad. Sci.* (1994), vol. 91, pp. 5022–5026.

Pierce catalog. (1994) pp. T159, T314–T315, Rockford, Illnois US.

*Principles and Practice of Immunoassay*, Chapter 5, "Immunoassay Design and Optimization".

*Principle and Practice of Immunoassay*, Chapter 13, "Heterogeneous Fluoroimmunoassay".

Sambrook et al. *Molecular Cloning: A laboratory manual* (1989) $2^{nd}$ ed. Lake Press, NY.

Service, R. "Radio tags speed compound synthesis" *Science*, (Oct. 27, 1995) vol. 270, p. 577.

Sproat, BS and DM Brown "A new linkage for solid phase synthesis of oligodeoxyribonucleotides" *Nucleic Acids Research* (1985) vol. 13, pp. 2979–2987.

Urdea et al. "A comparison on non–radioisotopic hybridization assay method using flouroscent, chemiluminescent and enzyme labeled synthetic oligodeoxyribonucleotide probes" *Nucleic Acids Research*, (1988) vol. 16, No. 11 pp. 4937–4956.

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
       (A) LENGTH: 120 base pairs
       (B) TYPE: nucleic acid
       (C) STRANDEDNESS: double
       (D) TOPOLOGY: linear (ii) MOLECULE TYPE: DNA (genomic)

(ix) FEATURE:
       (A) NAME/KEY: CDS
       (B) LOCATION: 1..120

(xi) SEQUENCE DESCRIPTION: SEQ ID NO:1:

```
ATG ACT GAG TAC AAA CTG GTG GTG GTT GGA GCA GGT GGT GTT GGG AAA         48
Met Thr Glu Tyr Lys Leu Val Val Val Gly Ala Gly Gly Val Gly Lys
 1               5                  10                  15

AGC GCA CTG ACA ATC CAG CTA ATC CAG AAC CAC TTT GTA GAT GAA TAT         96
Ser Ala Leu Thr Ile Gln Leu Ile Gln Asn His Phe Val Asp Glu Tyr
                20                  25                  30

GAT CCC ACC ATA GAG GTG AGG CCC                                        120
Asp Pro Thr Ile Glu Val Arg Pro
            35                  40
```

(2) INFORMATION FOR SEQ ID NO:2:

(i) SEQUENCE CHARACTERISTICS:
       (A) LENGTH: 40 amino acids
       (B) TYPE: amino acid
       (D) TOPOLOGY: linear (ii) MOLECULE TYPE: protein (xi) SEQUENCE DESCRIPTION: SEQ ID NO:2:

```
Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
                20                  25                  30

Asp Pro Thr Ile Glu Val Arg Pro
            35                  40
```

(2) INFORMATION FOR SEQ ID NO:3:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "chemically synthesized
           oligonucleotide corresponding to residues 3-22 of exon"

(xi) SEQUENCE DESCRIPTION: SEQ ID NO:3:

GACTGAGTAC AAACTGGTGG                                                   20

(2) INFORMATION FOR SEQ ID NO:4:

(i) SEQUENCE CHARACTERISTICS:
       (A) LENGTH: 20 base pairs (B) TYPE: nucleic acid
            (C) STRANDEDNESS: single
            (D) TOPOLOGY: linear (ii) MOLECULE TYPE: other nucleic acid
        (A) DESCRIPTION: /desc = "chemically synthesized
            oligonucleotide corresponding to residues 111-91 of
            exon with biotin attached"

(xi) SEQUENCE DESCRIPTION: SEQ ID NO:4:

CTCTATGGTG GGATCATATT                                              20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "chemically synthesized
            oligonucleotide corresponding to residues 14-33 of exon"

(xi) SEQUENCE DESCRIPTION: SEQ ID NO:5:

AACTGGTGGT GGTTGGAGCA                                              20

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:6:

AACTGGTGGT GGTTGGAGCA C                                            21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:7:

AACTGGTGGT GGTTGGAGCA G                                            21

(2) INFORMATION FOR SEQ ID NO:8:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "top strand of the target
            gene"

(xi) SEQUENCE DESCRIPTION: SEQ ID NO:8:

ATGACTGAGT ACAAACTGGT GGTGGTTGGA GCAGGTGGTG TTGGGAAAAG CGCACTGACA       60

ATCCAG                                                                          66

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:9:

CTCCAACCAC CACCAGTTTG TTT                                                       23

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:10:

CTCTATGGTG GGATCATATT                                                           20

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:11:

AAGCGCTTTT CCCAACACCA CC                                                        22

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:12:

AAGCGCTTTT CCCAACACCA CG                                                        22

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:13:

```
AAACTGGTGG TGGTTGGAGC AC                                                  22
```

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:14:

```
AAACTGGTGG TGGTTGGAGC AG                                                  22
```

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:15:

```
GTGTTGGGAA AAGCGCACTG ACCC                                                24
```

(2) INFORMATION FOR SEQ ID NO:16:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:16:

```
AACAGTGCGC TTTTCCCAAC ACCACCTGCT CCAACCACCA CCAGTTTTTT                    50
```

(2) INFORMATION FOR SEQ ID NO:17:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:17:

```
AACAGTGCGC TTTTCCCAAC ACCACGTGCT CCAACCACCA CCAGTTTTTT                    50
```

(2) INFORMATION FOR SEQ ID NO:18:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

-continued

```
    (xi) SEQUENCE DESCRIPTION: SEQ ID NO:18:

AAAACTGGTG GTGGTTGGAG CACGTGGTGT TGGGAAAAGC GCACTGACCC           50

(2) INFORMATION FOR SEQ ID NO:19:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "bottom strand of target
            DNA"

(xi) SEQUENCE DESCRIPTION: SEQ ID NO:19:

CTGGATTGTC AGTGCGCTTT TCCCAACACC ACCTGCTCCA ACCACCACCA TTTTGTACTC    60

AGTCAT                                                              66

(2) INFORMATION FOR SEQ ID NO:20:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:20:

AAAACTGGTG GTGGTTGGAG CAGGTGGTGT TGGGAAAAGC GCACTGACCC           50
```

MULTIPLEX ASSAY FOR NUCLEIC ACIDS EMPLOYING TRANSPONDERS

This application is a continuation-in-part of U.S. Ser. No. 08/564,851, filed on Nov. 30, 1995, now abandoned.

BACKGROUND OF THE INVENTION

This invention relates to materials and methods for detecting nucleic acids in samples and, more particularly, to solid phase assays wherein transponders are associated with the beads constituting the solid phase, nucleic acid probes are bound to the surface of the particles and data concerning the assay is encoded on the transponders.

Solid phase assays have been used to determine the presence of nucleic acids, including deoxyribonucleic acids (DNA), ribonucleic acids (RNA) and their modified forms. Solid-phase assays can be applied to nucleic acids either in simple buffers, or in biological fluids, such as blood, serum, plasma, saliva, urine, tissue homogenates, and many others.

In solid phase assays, small beads, or microparticles, are used as the solid phase to capture the analyte. Solid-phase microparticles can be made of different materials, such as glass, plastic, latex, depending on the particular application. Some beads are made of ferromagnetic materials to facilitate their separation from complex suspensions or mixtures.

In conventional solid-phase assays, the solid phase mainly aids in separating molecules that bind to the solid phase from molecules that do not bind to the solid phase. Separation can be facilitated by gravity, centrifugation, filtration, magnetism, immobilization of molecules onto the surface of the vessel, etc. The separation may be performed either in a single step in the assay or, more often, in multiple steps.

Often, there is a need to perform two or more different assays on the same sample, most of the time in a single vessel and at about the same time. Such assays are known in the art as multiplex assays. Multiplex assays are performed to determine simultaneously the presence or concentration of more than one molecule in the sample being analyzed, or alternatively, several characteristics of a single molecule, such as, the presence of several epitopes on a single protein molecule.

One problem with conventional multiplex assays is that they typically cannot detect more than about five analytes simultaneously, because of difficulties with simultaneous detection and differentiation of more than about five analytes. In other words, the number of different analytes that may be assayed in a single solid phase assay is limited by the solid phase. The present inventions overcomes these difficulties by providing a method of electronic indexing for different analytes.

High-throughput methods for genetic sequence analysis are critical for identification of polymorphisms and mutations in genes. Often, the first step in a genetic analysis is the DNA amplification using the polymerase chain reaction (PCR) to prepare a relatively large quantity of template (target) DNA. Ligase chain reaction (LCR) has also been used to prepare a quantity of the target DNA. The more genes and mutations in the gene one wants to investigate, the more amplification reactions one needs to perform. While in principle several amplification reaction can be performed in a single test tube, the identification and separation of the products of the amplification has presented a difficulty. The present invention provides the means of identifying products of the PCR and LCR reactions, as well as separating the products after the amplification reaction. The principle is the indexing of the oligonucleotides used for amplification in PCR or LCR by means of electronic circuitry.

SUMMARY OF THE INVENTION

The present invention overcomes many of these problems by employing transponders associated with the solid phase beads to index the particles constituting the solid phase. Thus, each individual solid phase particle can be assigned a unique index number electronically encoded inside the particle, that can be retrieved at any time, e.g., at one time during the assay, at multiple times during the assay, or continuously during the assay. The index number may define the nucleotide sequence of the oligonucleotide deposited on the surface of the particle, the catalog number of a DNA fragment deposited on the particle, index numbers of chemical steps which were involved in the chemical synthesis of an oligonucleotide bound to the particle, or some other relevant characteristics of the deposited molecules.

In an electronically-indexed multiplex assay of this invention, two or more classes of transponders, each encoded with a different index number and constructed to bind a different nucleic acid sequence, are incubated with the sample in a single vessel. After necessary washes, incubations and additions are performed, the solid phase is analyzed to detect a label indicative of binding of nucleic acid in the sample to the oligonucleotide on the transponder, such as fluorescence, color, radioactivity or the like. Solid phase analysis is either preceded or followed by decoding of the index numbers programmed on the transponders.

Determination of the label and decoding of the memory of the transponder can be done manually on two different instruments, such as a fluorometer and a dedicated scanner, although a single automated instrument that would perform both functions may be used. Such an instrument can be a modified fluorometer in which the scanner is mounted in the proximity of the fluorometer readout window, and reading the sample fluorescence and decoding the transponder are coordinated by a central computer. In addition, such an instrument can be equipped with an automated transport system for transponders.

In one aspect, the present invention provides an electronically-indexed solid phase particle for use in solid phase assays for nucleic acids, comprising a transponder and a nucleic acid sequence attached to the transponder.

In another aspect, the present invention provides a method for detecting nucleic acids in a sample, using solid phase particles having transponders.

In another aspect, the present invention provides kits for detecting nucleic acids in samples, comprising assay vessels, at least one transponder having a nucleic acid probe bound to the transponder, and a labeled reagent to detect binding of sample nucleic acids to the probe.

In yet another aspect, the present invention provides also a method to amplify nucleic acids (DNA, RNA) by PCR or LCR yielding a product DNA which is immobilized on the transponder. The transponder's function is to store data that identify the sequence of one of the two primers (in PCR) or one of the four oligonucleotides (in LCR). In an assay, the fluorescence or the color of the solid phase indicates that the amplification with a given primer or oligonucleotide took place, and the data stored on the transponder can be decoded at any moment of the assay to identify the product of the amplification.

DETAILED DESCRIPTION OF THE INVENTION

Figure 1A:
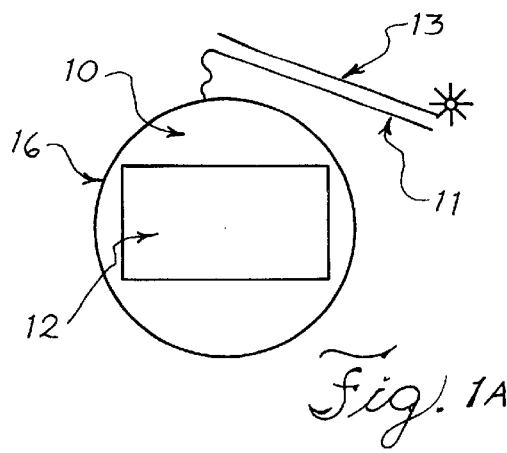
FIG. 1A is a schematic representation of a simple assay of this invention.

FIG. 1A depicts a simple assay of the invention. A solid phase particle 10, with a transponder 12 is derivatized by attaching an oligonucleotide probe 11 to the outer surface 16 of the particle 10. Information concerning the assay, e.g., an index number identifying the patient, is encoded on the transponder, either by the manufacturer of transponder, or by the user with a remote read/write scanner device (not shown). Sample containing target nucleic acid 13 is treated to label all of the nucleic acid therein. The derivatized particle 10 is placed in a sample, and the sample is heated to cause nucleic acids to dissociate. The sample is then cooled under controlled conditions to cause the nucleic acids to anneal. Target nucleic acids 13 complementary to the oligonucleotide probe 11 anneal to the probe 11. The particle 10 is thoroughly washed to remove unbound components. The labeled target nucleic acid 13 bound to the probe 11 is detected with a fluorometer to identify those transponders 12 that have target nucleic acid 13 bound thereto, and the transponder 12 is decoded using the scanner device (not shown) to retrieve the information encoded thereon.

The detection and decoding steps may be done separately or may be done simultaneously. Alternatively, the particles of many samples may be pooled into a vessel in no particular order with mixing allowed, and passed through a reader (not shown) that determines and records the fluorescence and, at the same time, decodes the index number recorded in the transponder 12. It is important to note that when encoding or reading data on a transponder, other transponders must be shielded by a metal barrier or other means to prevent the electromagnetic radiation from reaching such "non-target" transponders.

Figure 1B:
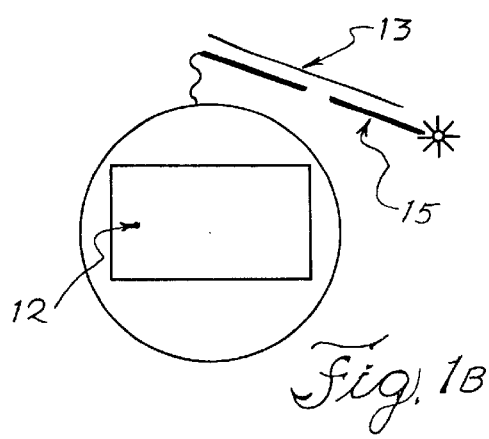
FIG. 1B is a schematic representation of a simple assay of this invention utilizing an alternative labeling technique.

In an alternative labeling technique, depicted in FIG. 1B, a second fluorescent-labeled oligonucleotide probe 15 complementary to a second sequence of the target nucleic acid 13 is added to the sample mixture, to specifically label transponders 12 to which target nucleic acids 13 have bound.

Figure 2A:
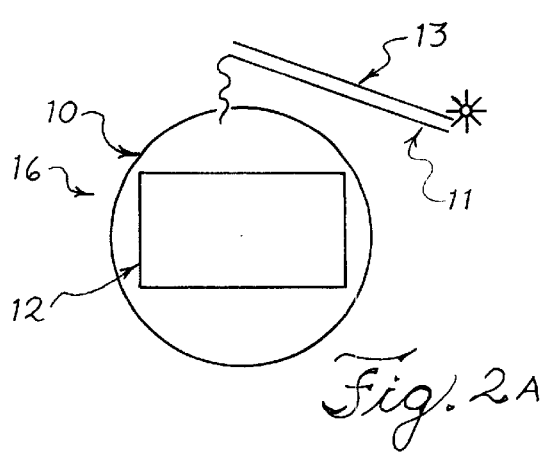
FIG. 2A and FIG. 2B are schematic representations of a multiplex assay of this invention.
Figure 2B:
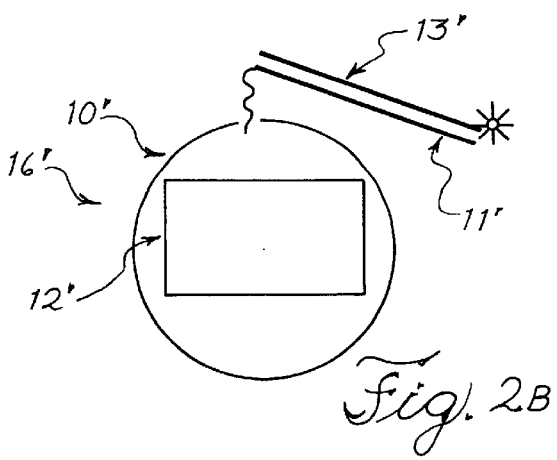

A multiplex assay according to this invention is conducted in a similar manner, as depicted in FIG. 2A and FIG. 2B, with two or more transponders 12 in each assay vessel (not shown) to detect more than one target nucleic acid 13 simultaneously. The transponders 12 are divided into two or more classes 12 and 12', each class having a distinct index number identifying the class, and each class having a different oligonucleotide probe 11 and 11' bound to the surface 16 of the particle 10 and 10'. Using each class of transponder 12, 12' is separately encoded, either by the manufacturer or by the user with a read/write scanner device (not shown), with an index number to identify, e.g., the sequence of the probe 11 bound to the surface 16 of the particle 10. Again, it is necessary to shield other, non-target transponders during the encoding process. The transponders 12, 12' are added to a sample, and the sample is heated to cause nucleic acids to dissociate. The sample is then cooled under controlled conditions to cause the nucleic acids to re-anneal. Target nucleic acid 13, 13' complementary to the respective probes 11, 11' anneals to the probes 11, 11'. The transponders 12, 12' are then washed thoroughly to remove unbound sample components and reagents. The labeled probes 15, 15' are detected with a fluorometer to identify those transponders 12, 12' that have target nucleic acids 13, 13' bound thereto, and the transponder 12, 12' is decoded using the scanner device (not shown) to retrieve the information encoded thereon. The detection and decoding steps may be done separately or may be done simultaneously. Alternatively, the particles 10, 10' may be pooled into a vessel in no particular order with mixing allowed, and passed through a reader (not shown) that determines and records the fluorescence and, at the same time, decodes the index number recorded in the transponder 12, 12'.

Figure 2C:
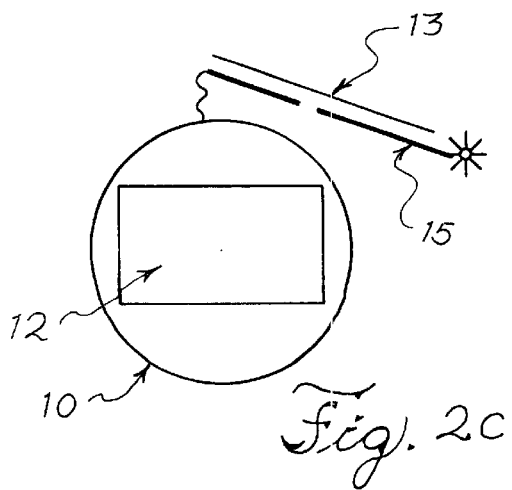
FIG. 2C and FIG. 2D are schematic representations of a multiplex assay of this invention utilizing an alternative labeling technique.
Figure 2D:
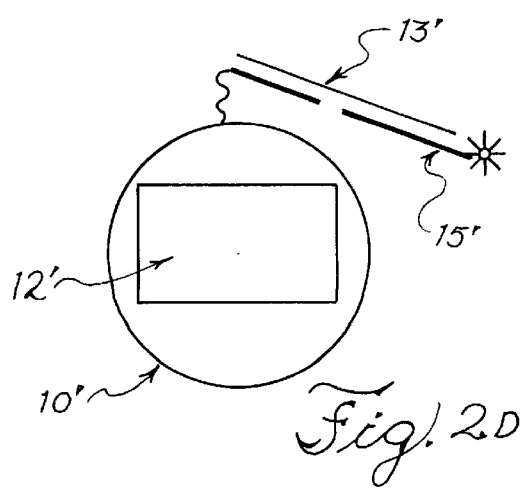

In an alternative labeling technique, depicted in FIG. 2C and FIG. 2D, second fluorescent-labeled oligonucleotide probes 15, 15' that bind to second sequences of the target nucleic acids 13, 13' are added to the sample vessel to bind to the target nucleic acids 13, 13'. Alternatively, the label may be a radioisotope, such as $^{32}P$, $^{35}S$, $^{125}I$, and the like. The label may also be a chemiluminescent label, such as a luminol derivative or an acridinium ester, that emits light upon oxidation of a substrate. The label may be an enzyme, such as alkaline phosphatase, catalyzing a reaction employing a precipitating fluorogenic substrate, e.g., attophos (JBL Scientific, San Luis Obispo, Calif.), a precipitating chromogenic substrate, e.g., 5-bromo-4-chloro-3-indolyl phosphate), or a chemiluminescent substrate, e.g., adamantyl 1,2-dioxetane phosphate (Tropix, New Bedford, Mass.). Finally, the label may be a bioluminescent enzyme such as luciferin.

The present multiplex assay can be applied to different types of nucleic acids, DNA, RNA, modified nucleic acids and analogs of nucleic acids (in particular protein-nucleic acids, PNAs). The analyte can be a complex of biomolecules, such as a virus particle, a nucleic acid-protein complex, or a nucleic acid-hapten complex. It is also evident that the target nucleic acid analyte, which is being monitored, can be present in a variety of forms, such as a solution in a simple buffer, but also in a complex biological fluid, such as blood, serum, urine, saliva, and many others. The target nucleic acid can be mixed with many other analytes that are simultaneously being assayed in the multiplex format. The purity of the nucleic acid deposited as a primary layer on the surface of the transponder can vary as well, from unpurified, partially purified to pure compounds.

The nucleic acids, their complexes and aggregates can be deposited as a primary layer on the surface of the transponder by a variety of means, including chemical conjugation to an active group on the support, direct chemical synthesis, combinatorial synthesis, adhesion or non-specific binding through hydrophobic interactions. The nucleic acid deposited as a primary layer on the surface of the transponder can be made in vivo, in an enzymatic reaction in vitro, or chemically synthesized. A preferred example of a product of an enzymatic reaction in vitro is the nucleic acid obtained from the polymerase chain reaction (PCR).

Figure 3:
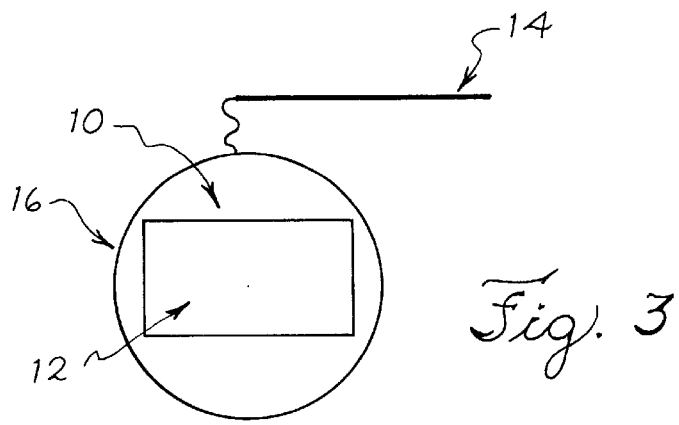
FIG. 3 is a diagram of a solid phase particle with a transponder, and a primary layer of a nucleic acid sequence attached to the surface thereof.

FIG. 3 depicts a solid phase particle 10 of the present invention, having a transponder 12, and a primary layer 14 of an oligonucleotide probe attached to the outer surface 16 of the particle 10.

A transponder is a radio transmitter-receiver activated for transmission of data by reception of a predetermined signal, and may also be referred to as a microtransponder, radiotransponder, radio tag, transceiver, etc. The signal comes from a dedicated scanner that also receives and processes the data sent by the transponder. The scanner function can be combined with the write function, i.e., the process of encoding the data on the transponder. Such a combination instrument is referred to as a scanner read/write device. An advantage of the transponder-scanner systems is that the two units are not electrically connected by wire, but are coupled inductively, i.e. by the use of electromagnetic radiation, typically in the range from 5–1,000 kHz, but also up to 1 GHz and higher.

Figure 4:
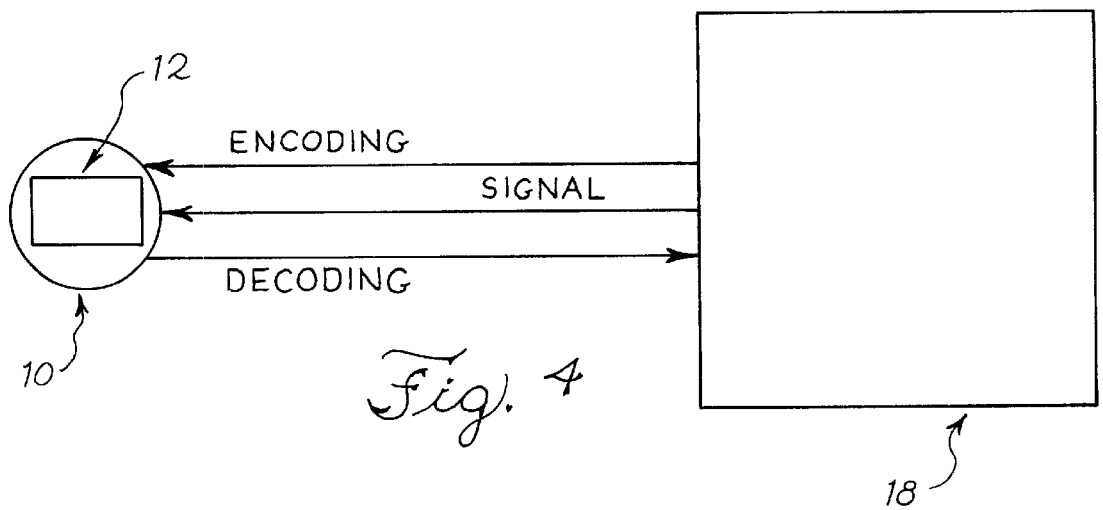
FIG. 4 is a schematic diagram of the signal pathway for encoding and encoding data on the transponders.

FIG. 4 is a flow chart illustrating the communication between the transponder 12 and a remote scanner read/write device 18. The transponder 12 is encoded and/or decoded with data sent by electromagnetic waves from a remote scanner read/write device 18, unless the transponders 12 have been encoded by the manufacturer. After the assay steps are completed, the beads 10 are analyzed to detect the presence of a label indicative of binding of analyte and the transponders 12 are decoded. The scanner 18 sends a signal to the transponder 12. In response to the signal, the transponder 12 transmits the encoded data to the scanner 18.

Some transponders similar to those used in the present invention are available commercially. BioMedic Data Systems Inc. (BMDS, 255 West Spring Valley Ave., Maywood, N.J.) manufactures a programmable transponder for use in laboratory animal identification. The transponder is implanted in the body of an animal, such as a mouse. The transponder is glass-encapsulated to protect the electronics inside the transponder from the environment. One of the transponders manufactured by this corporation, model IPTT-100, has dimensions of 14×2.2×2.2 mm and weight of 120 mg. The transponder is user-programmable with up to 16 alphanumeric characters, the 16th letter programmable independently of the other 15 letters, and has a built-in temperature sensor as well. The electronic animal monitoring system (ELAMS) includes also a scanner read/write system, such as the DAS-501 console system, to encode or read data on/from the transponder. The construction of the transponder and scanner is described in U.S. Pat. Nos. 5,250,944, 5,252,962 and 5,262,772, the disclosures of which are incorporated herein by reference. Other similar transponder-scanner systems include a multi-memory electronic identification tag (U.S. Pat. No. 5,257,011) by AVID Corporation (Norco, Calif.) and a system made by TEMIC-Telefunken (Eching, Germany). AVID's transponder has dimensions of 1 mm×1 mm×11 mm, and can encode 96 bits of information, programmable by the user. The present invention can be practiced with different transponders, which might be of different dimensions and have different electronic memory capacity.

The commercially available transponders are relatively large in size. The speed at which the transponders may be decoded is limited by the carrier frequency and the method of transmitting the data. In typical signal transmission schemes, the data are encoded by modulating either the amplitude, frequency or phase of the carrier. Depending on the modulation method chosen, compression schemes, transmission environment, noise and other factors, the rate of the signal transmission is within two orders of magnitude of the carrier frequency. For example, a carrier frequency of 1,000 Hz corresponds to rates of 10 to 100,000 bits per second (bps). At the rate of 10,000 bps the transmission of 100 bits will take 0.01 sec. The carrier frequency can be several orders of magnitude higher than 1,000 Hz, so the transmission rates can be proportionally higher as well.

Therefore, the limiting factor in the screening process is the speed at which the transport mechanism carries the transponders through the read window of the fluorometer/scanner device. The rate of movement of small particles or cells is $10^4$–$10^5$ per second in state-of-the-art flow cytometers. A flow cytometer may be used to practice the present invention, if two conditions are met: (1) the transponders are small enough to pass through the flow chamber, and (2) the design of the flow chamber of the flow cytometer is modified to include an antenna and a read/write scanner device for collecting the electromagnetic radiation emitted by transponders.

Figure 5:
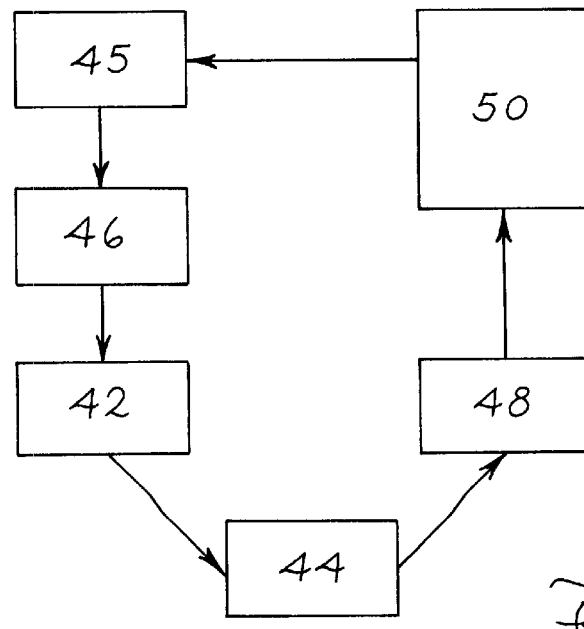
FIG. 5 is a schematic representation of a miniature transponder.
Figure 6:
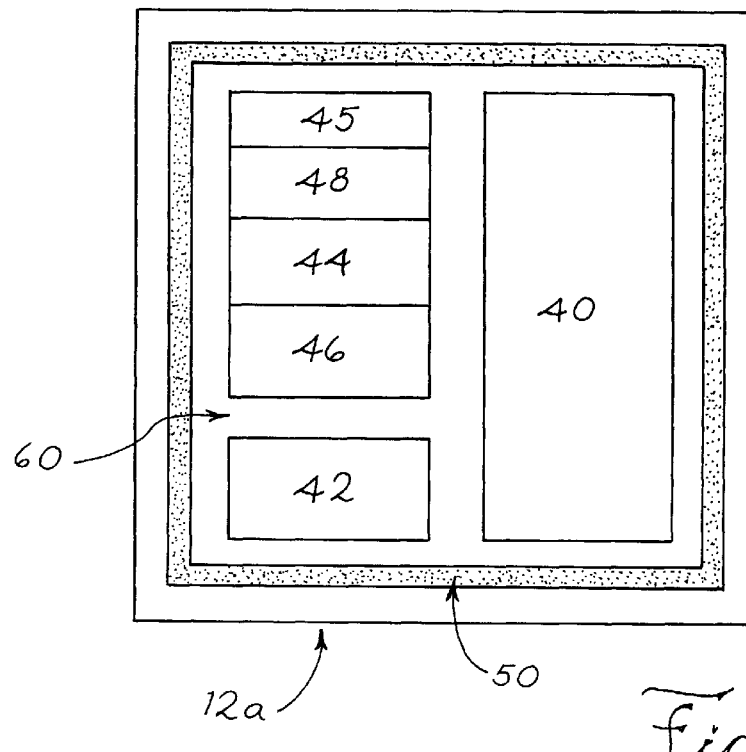
FIG. 6 is a plan view of a miniature transponder.

A miniature transponder is depicted in FIGS. 5 and 6. The source of the electrical power for the transponder 12a is at least one photovoltaic cell 40 within the transponder 12a, illuminated by light, preferably from a laser (not shown). The same light also induces the fluorescence of fluorogenic molecules immobilized on the surface of the transponder 12a. The transponder 12a includes a memory element 42 that may be of the EEPROM type, or the ROM type. The contents of the memory is converted from the digital form to the analog form by a Digital-to-Analog converter 44 mounted on the transponder 12a. The signal is amplified by an amplifier 45, mixed with the carrier signal produced by an oscillator 48, and emitted to the outside of the transponder 12a by an antenna 50.

In an alternative embodiment, the signal from the scanner (not shown) is transmitted to the transponder 12a by modulating the intensity of the light illuminating the transponder 12a, which also serves to actuate the photovoltaic cell power source 40.

The contents of the miniature transponder memory can be permanently encoded during the manufacturing process of the transponder, different batches of transponders being differently encoded. Preferably, the memory of the transponder is user-programmable, and is encoded by the user just before, during, or just after the biological material is deposited on the surface of the transponder. A user-programmable transponder 12a must have the "write" feature enabled by the antenna 50, amplifier 44 and the Analog-to-Digital converter 46 manufactured on the transponder 12a, as well as the dedicated scanner/write device 27.

The advantages of the transponder of FIGS. 5 and 6 are several-fold. First, the transponder dimensions are reduced relative to a conventional transponder, because most of the volume of a conventional transponder is occupied by the solenoid. The design discussed above will enable the production of cubic transponders on the order of 0.01 to 1.0 mm as measured along a side of the cube, preferably 0.05 to 0.2 mm.

Second, a large number of transponders can be manufactured on a single silicon wafer. As depicted schematically in FIG. 6, a silicon wafer 60 is simply cut to yield active transponders 12a. Third, the transponder, according the new design, will not need the glass capsule as an enclosure, further reducing the size of the transponder. Silicone dioxide ($SiO_2$) would constitute a significant portion of the surface of the transponder, and $SiO_2$ has chemical properties like glass in terms that allow derivatization or immobilization of biomolecules. Alternatively, the transponder may be coated with a variety of materials, including plastic, latex and the like.

Finally, most importantly, the narrow focus of the beam of the laser light would enable only one transponder to be active at a time during the decoding step, significantly reducing noise level. Advanced user-programmability is desirable as well, and preferably, various memory registers are addressable independently, i.e., writing in one register does not erase the contents of other registers.

Figure 7:
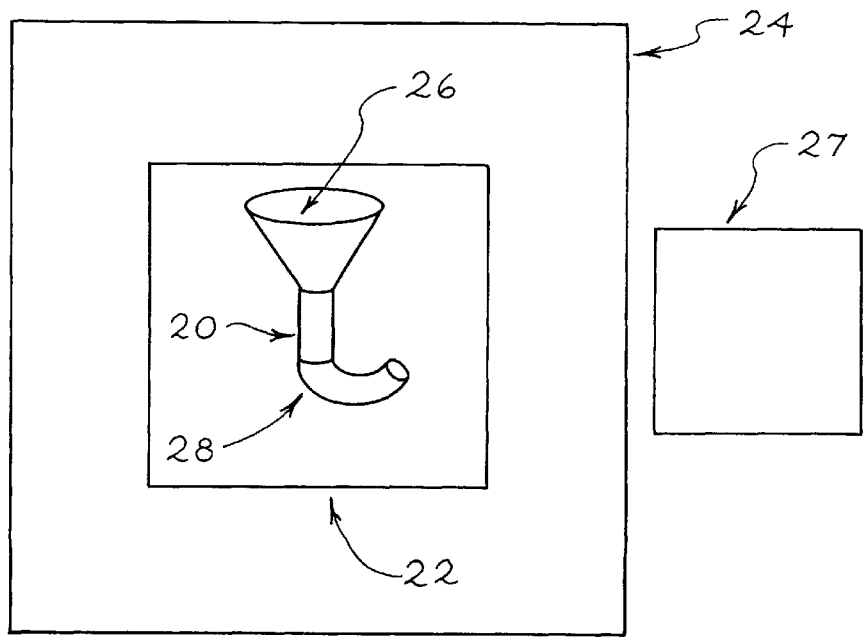
FIG. 7 is a plan view of a transport system/analytical instrument for implementing this invention.

FIG. 7 shows the analytical instrumentation and transport system used in an embodiment of the present invention. A quartz tube 20 is mounted in the readout window 22 of a fluorometer 24. The quartz tube 20 is connected to a metal funnel 26. The length of the quartz tube 20 is similar to the dimensions of the transponder 12. Transponders 12 are fed into the metal funnel 26, and pass from the funnel 26 into the quartz tube 20, where the fluorescence is read by the fluorometer 24 and the transponder 12 is decoded by the scanner 27, and then exit through a metal tube 28 and are conducted to a collection vessel (not shown). The metal funnel 26 and metal tube 28 are made of metal shield transponders 12 outside of the read window 22 by shielding from the electromagnetic signal from the scanner 27. This shielding prevents the scanner signal from reaching more than one transponder 12, causing multiple transponders 12 to be decoded.

Minimal modification of the fluorometer 24 would be needed in the vicinity of the location that the tube occupies at the readout moment to allow for positioning of the transponder reading device. To assure compatibility with existing assays, the glass surrounding the transponder could be coated or replaced with the type of plastic currently used to manufacture beads.

Figure 8:
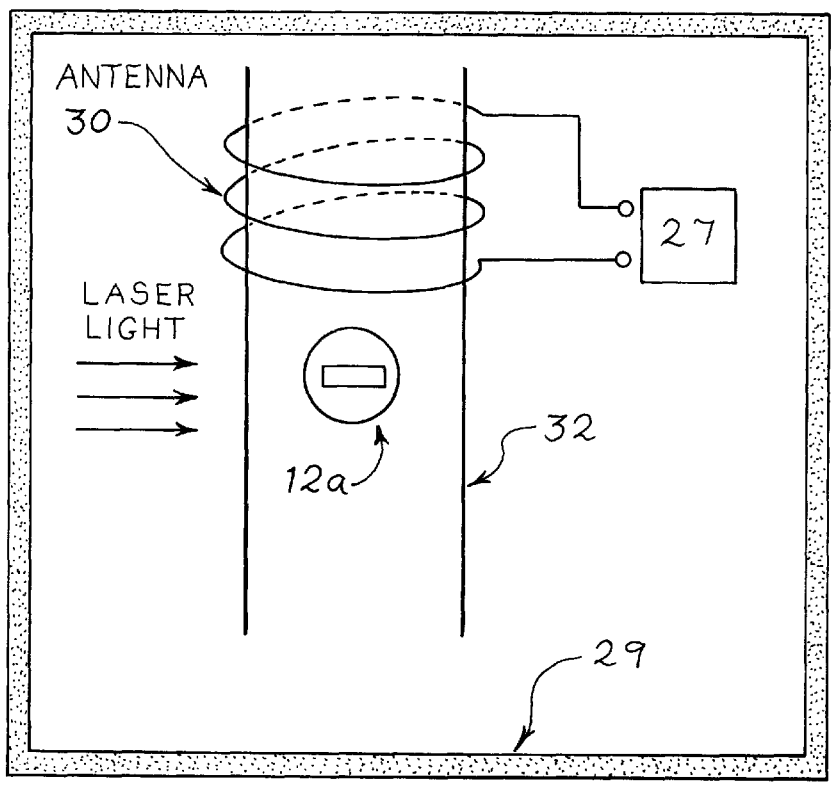
FIG. 8 is a plan view of modified flow cytometer for high speed analysis of solid phase particles of this invention.

In a preferred design, depicted in FIG. 8, a metal coil antenna 30 is wrapped around the flow cell 32 of a flow cytometer 29. The transponders 12 pass through the flow cell 32, and are decoded by the scanner device 27. The signal carrying the data sent from the transponders 12 is processed by the scanning device 27. As the transponders 12 are decoded, fluorescence from the transponders 12 is detected and analyzed by the flow cytometer 29.

Figure 9:
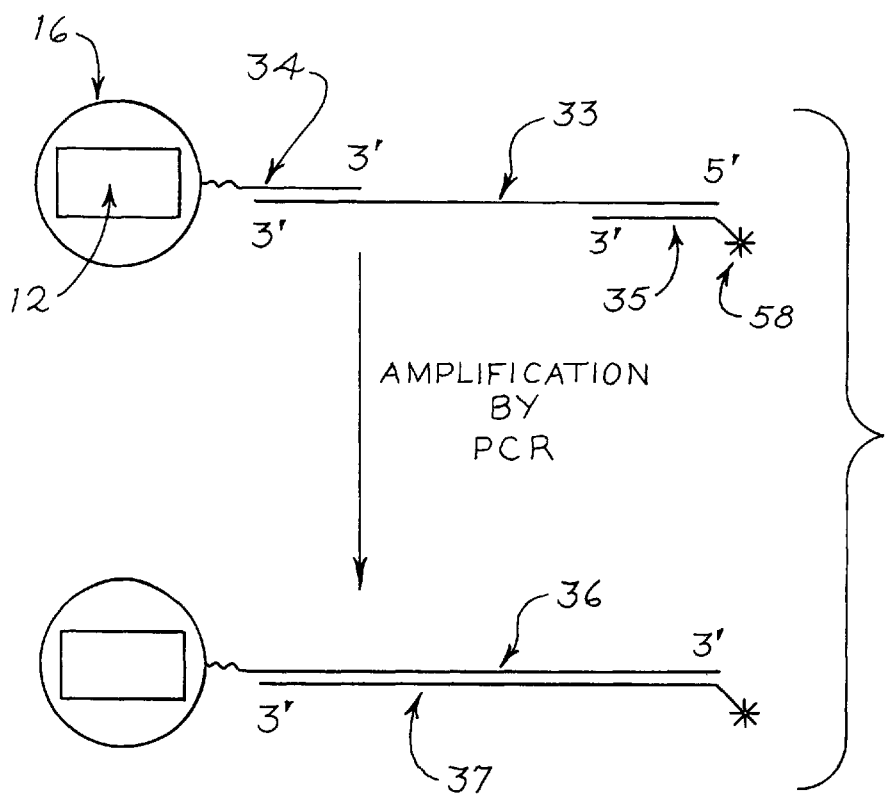
FIG. 9 is a diagram of PCR amplification on transponders.

The principle of the PCR amplification on transponders is illustrated in FIG. 9. The template 33 is a single-stranded nucleic acid. A primer 34 contains the sequence complementary to a part of the DNA template 33 sequence. The 5' primer is attached to the solid phase 16 comprising the transponder 12 through a linker. The other primer 35 has the sequence identical to a part of the template 33. The primer 35 is derivatized with a fluorophore 58. The following reagents: template 33, primer 34 conjugated to the solid phase 16, the primer 35 and a thermostable DNA polymerase are added to the standard PCR buffer and several cycles of amplification are performed. A single cycle of amplification involves the heating the reaction mixture to denature the nucleic acids in the reaction, cooling to specifically anneal the primers to the template, and the chain extension reaction with a thermostable DNA polymerase. Mixing of the contents of the reaction vessel is desired. The resulting product of the amplification are two DNA strands, 36 and 37, forming the fluorophore-containing double-stranded DNA attached to the solid phase 16. Next, to determine whether the sequences identical or complementary to the primer sequences were present in the template, the amount of the PCR product is quantitated by measuring the fluorescence of the solid phase particle 16 comprising the transponder 12, and the serial number of the transponder is read to identify the sequence of primer 34, and possibly to identify other information related to the assay.

Figure 10A:
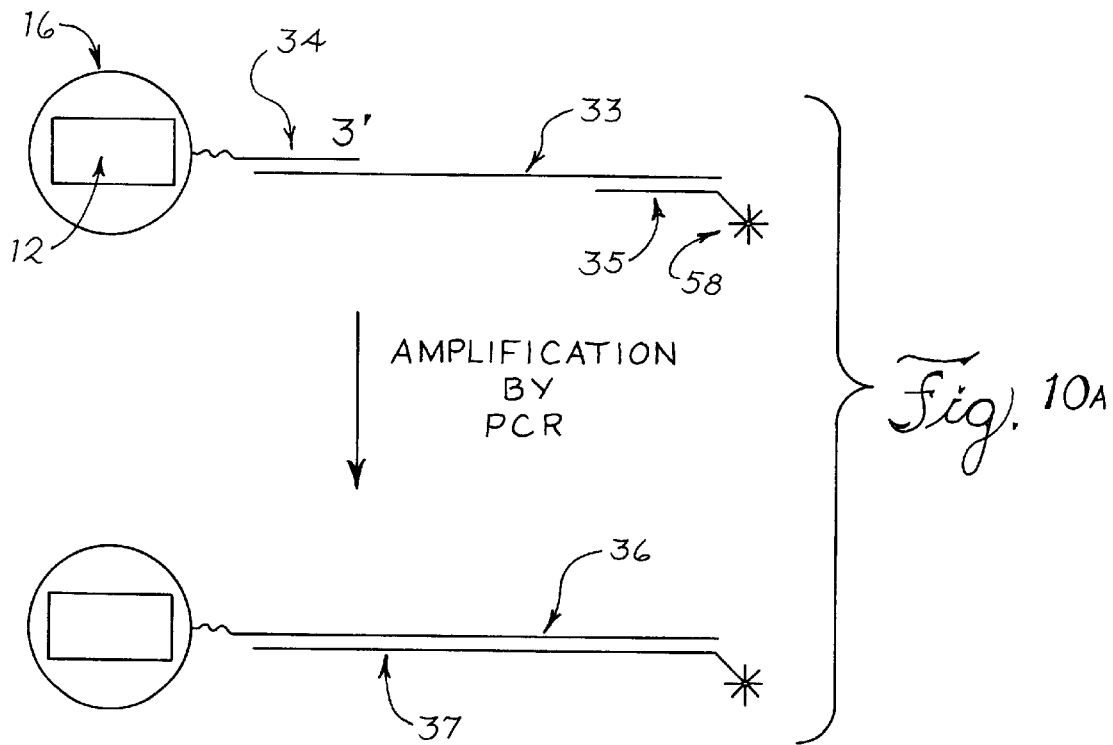
FIG. 10A and FIG. 10B are diagrams of a multiplex assay employing the PCR amplification on the transponders.
Figure 10B:
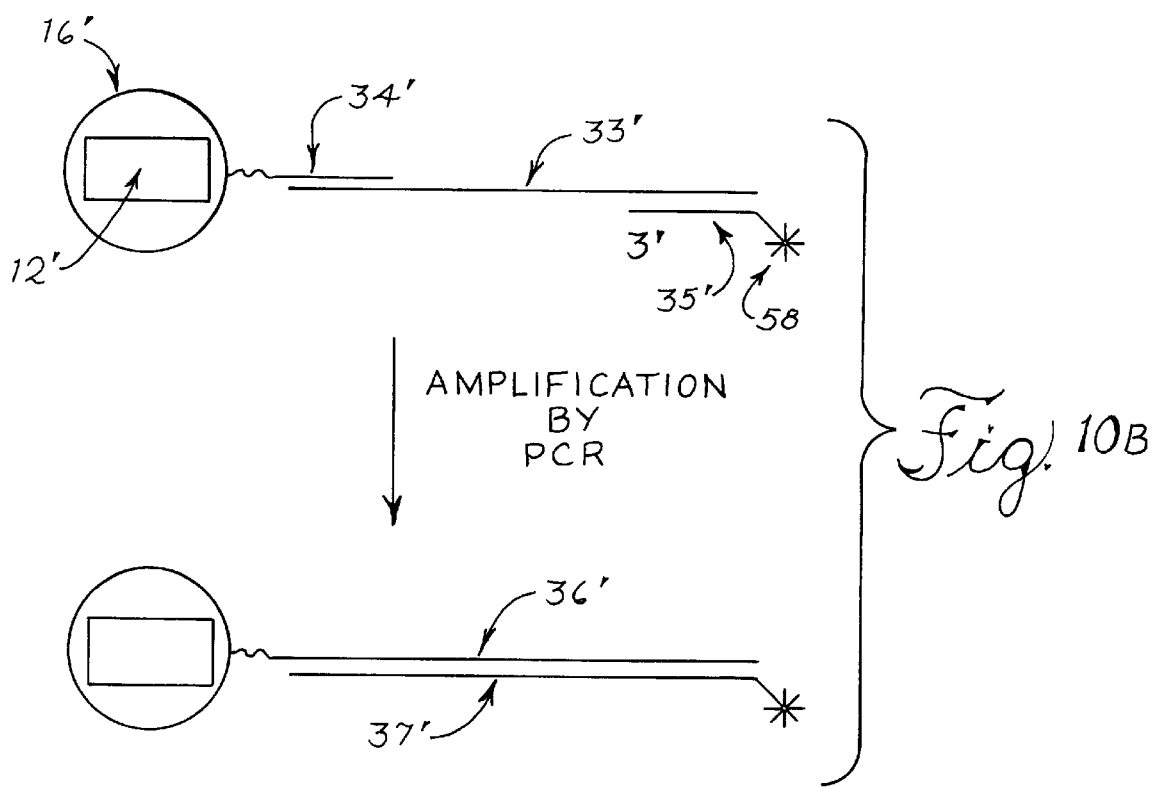

Multiple primers and multiple transponders can be used for more complex genetic analyses according to this invention. The multiplex assay with two classes of transponders is depicted in FIG. 10A and FIG. 10B. Each class of transponders, 12 and 12', is comprised within two classes of solid phase particles, 16 and 16', and has a unique index number characterizing the class encoded within the transponder. In one implementation of this invention, the index number defines the sequence of the oligonucleotide primer attached to the solid phase particle. The class 16 of solid phase particles is derivatized with oligonucleotide primer 34, and the class 16'—with primer 34'. The primers are specific for the two template nucleic acid molecules, 33 and 33', correspondingly. Two other PCR primers, 35 and 35', derivatized with a fluorophore 58, and specific for templates 33 and 33', correspondingly, are implemented in the single PCR amplification reaction with the said solid phase particles and nucleic acid templates. After the PCR amplification, the solid phase particles are washed and analyzed for fluorescence, and their index number is electronically decoded, and associated with the fluorescence measurement. Thus, the assay provides the information about the presence of two different template nucleic acids in the sample.

It is evident to a person skilled in the art that the number of the solid phase particles in the multiplex assay employing PCR can be greater than two, and limited only by the capabilities to manufacture the transponders in quantity, provided that sufficient care is taken to assure the specificity of the amplification in the single test tube PCR reaction. It is also evident to a person skilled in the art that one type of the template nucleic acid can be used in the multiplex PCR-based assay (i.e. template 33 can be the same as 33'). In such case, the assay provides multiple reads for the multiple genetic determinants in one nucleic acid template. Yet in another implementation of the multiplex PCR-based assay on a single template, one type of the primer derivatized with a fluorophore can be used (i.e. primer 35 can be the same as 35'). In this case, the assay provides the genetic determinants for this part of the template which is downstream (or 3') from the primer 35 site.

Figure 11:
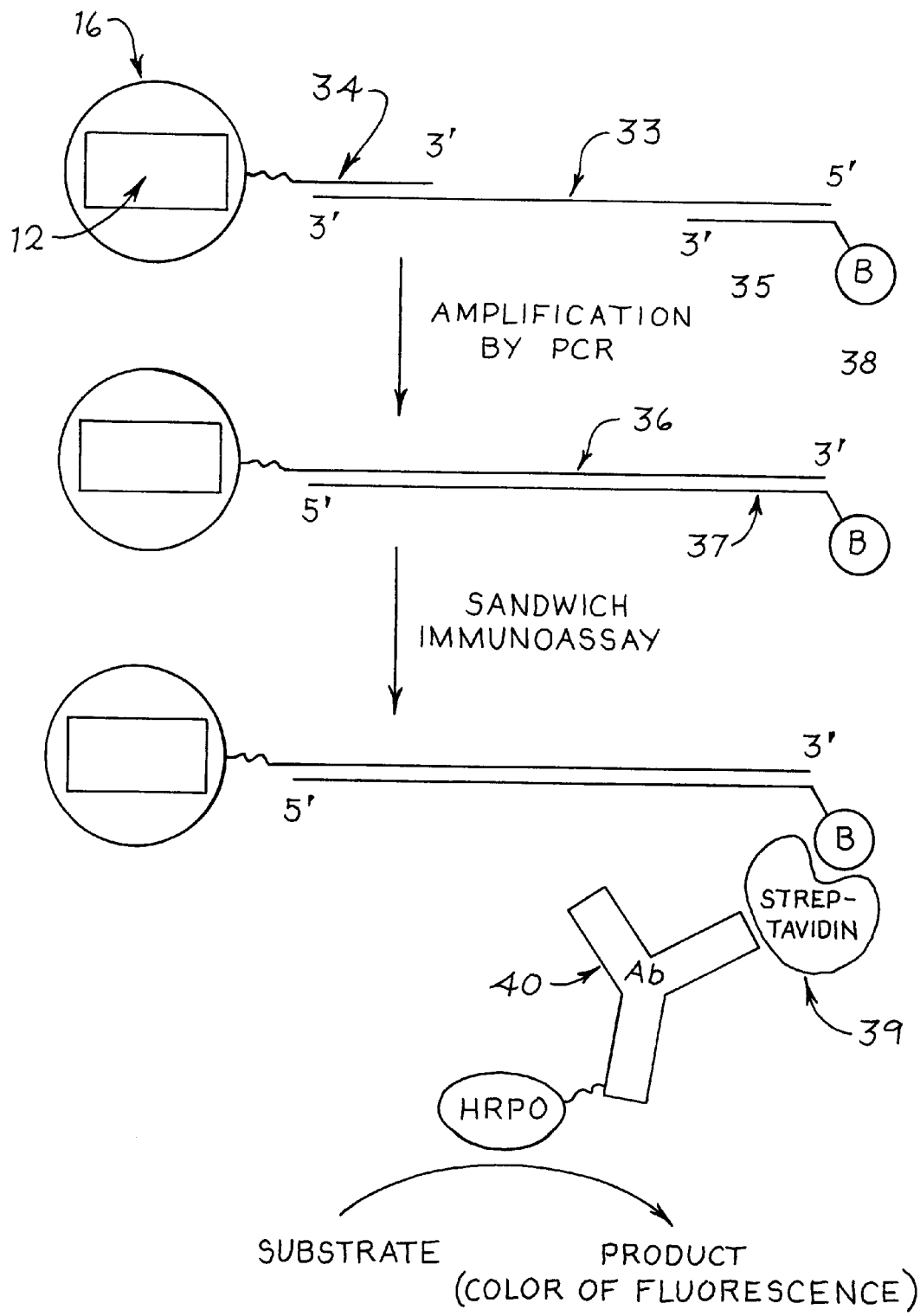
FIG. 11 is a diagram of a sandwich immunoassay employing PCR to detect nucleic acids.

An alternative detection system is presented in FIG. 11. Here, a sandwich immunoassay configuration is used to enhance the detection of the PCR product. The system employs oligonucleotide primer 34 immobilized on solid phase 16 comprising the transponder 12, and oligonucleotide primer 35 conjugated to biotin 38, preferably at the 5' end of primer 35. After the PCR amplification with template 33, the biotinylated product of the reaction, single stranded DNA 37, attached to the solid phase by forming double-stranded DNA complex with the other single-stranded product of PCR 36, is detected in a sandwich assay. The sandwich contains the product double-stranded DNA, biotin, streptavidin 39, anti-streptavidin antibody conjugated to horseradish peroxidase 40 (HRPO) or another suitable enzyme. This enzyme catalyses a reaction with a fluorogenic or chromogenic substrate. The amount of the product of the reaction indicates the amount of the DNA amplification product, and the presence or absence of the primer sequences in the template DNA.

The sandwich is formed by a serial addition of reagents. After the PCR amplification, the solid phase 16 is washed to remove unbound primer, reagents and by-products of PCR. Then, streptavidin 39 is added, incubated under conditions to allow it to bind to biotin 38 immobilized on solid support 16, and the solid phase 16 is washed to remove the unbound streptavidin. The anti-streptavidin antibody-HRPO conjugate 40 is then added, incubated under conditions to allow it to bind to streptavidin 39 immobilized on solid support 16, and the solid phase is washed again to remove the unbound antibody conjugate. The substrate for HRPO is then added to the reaction and incubated for the time sufficient for the enzymatic reaction to take place. The substrate can be either chromogenic, or fluorogenic, or chemiluminescent. The product of the reaction is quantified by measuring the color, fluorescence or chemiluminescence generated in the reaction.

Figure 12A:
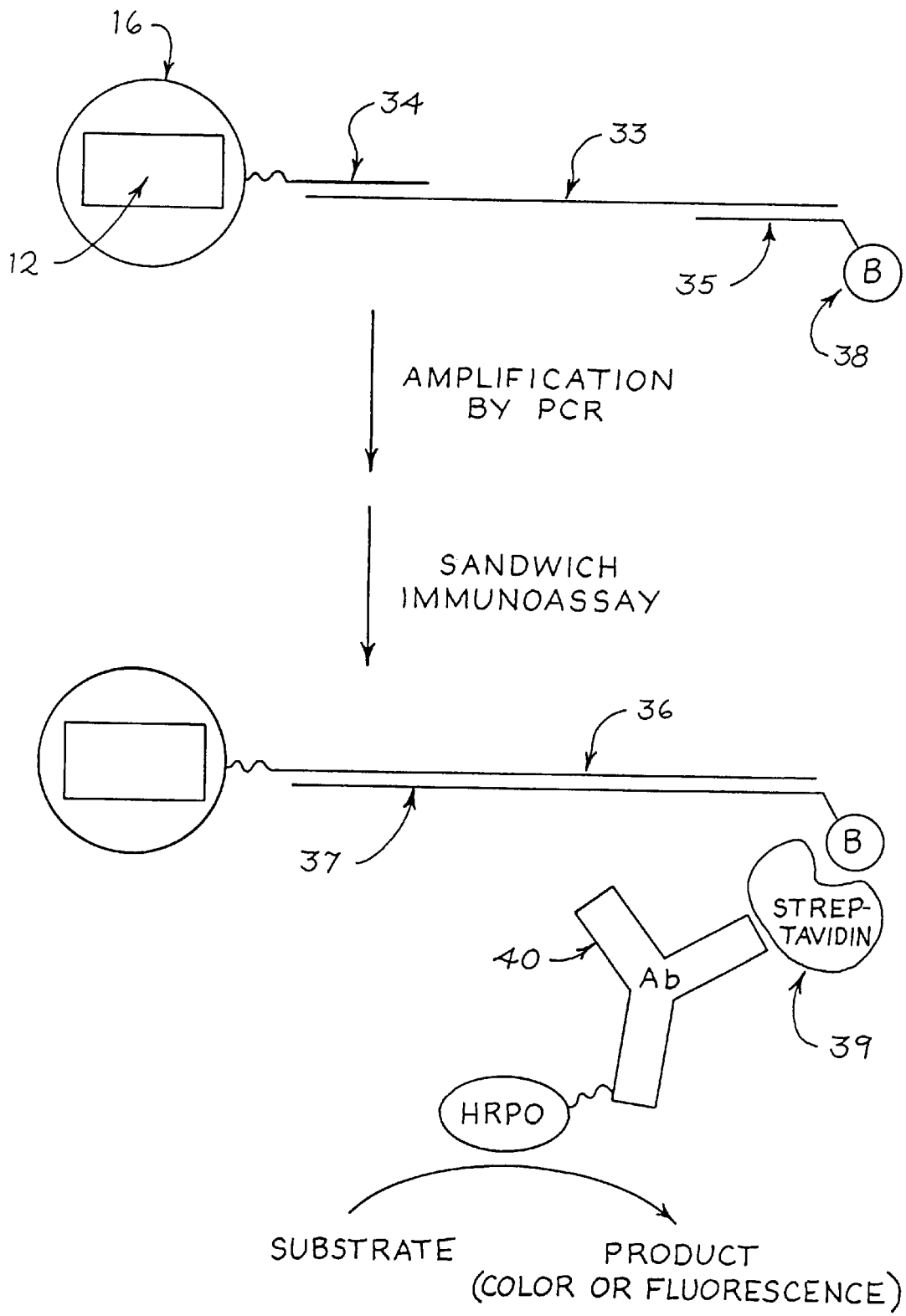
FIG. 12A and FIG. 12B are diagrams of a PCR-based multiplex assay followed by sandwich immunoassay detection.
Figure 12B:
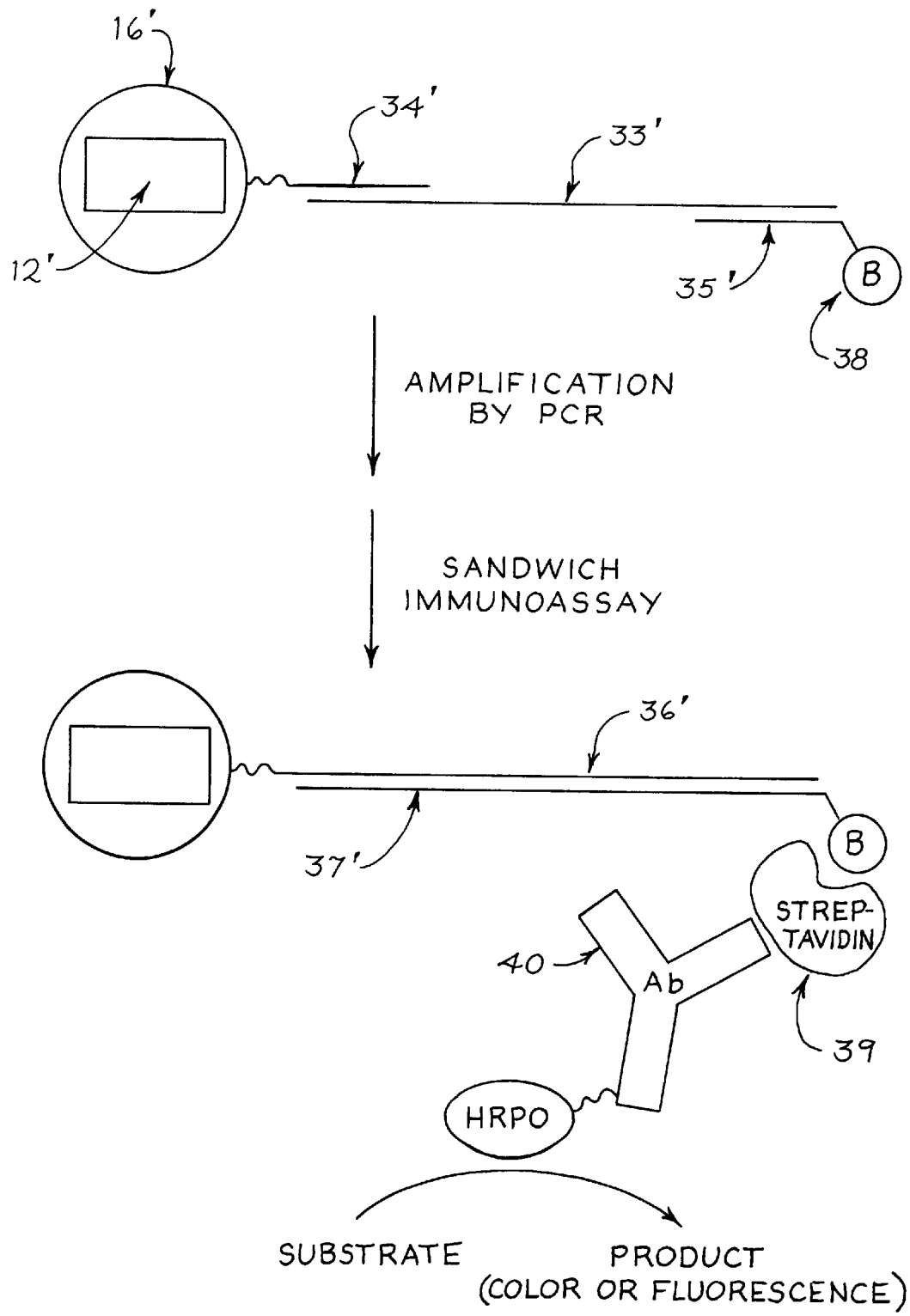

The sandwich assay format can be used in a multiplex format as depicted in FIG. 12A and FIG. 12B for two template nucleic acids 33 and 33'. In this assay, two pairs of primers are used, oligonucleotides 34 and 34' attached to the solid phase 16 and 16' which comprises transponders 12 and 12', respectively, and oligonucleotide primers 35 and 35' which are conjugated to biotin 38. After the PCR amplification, the reagents for the sandwich assay are added sequentially in the following order: streptavidin 39, wash, anti-streptavidin antibody conjugated to HRPO 40, wash, and the substrate. The color, fluorescence or chemiluminescence of the product of the enzymatic reaction is measured, and the index number of the transponders 12 and 12' is decoded, completing the PCR-based multiplex sandwich assay.

Figure 13:
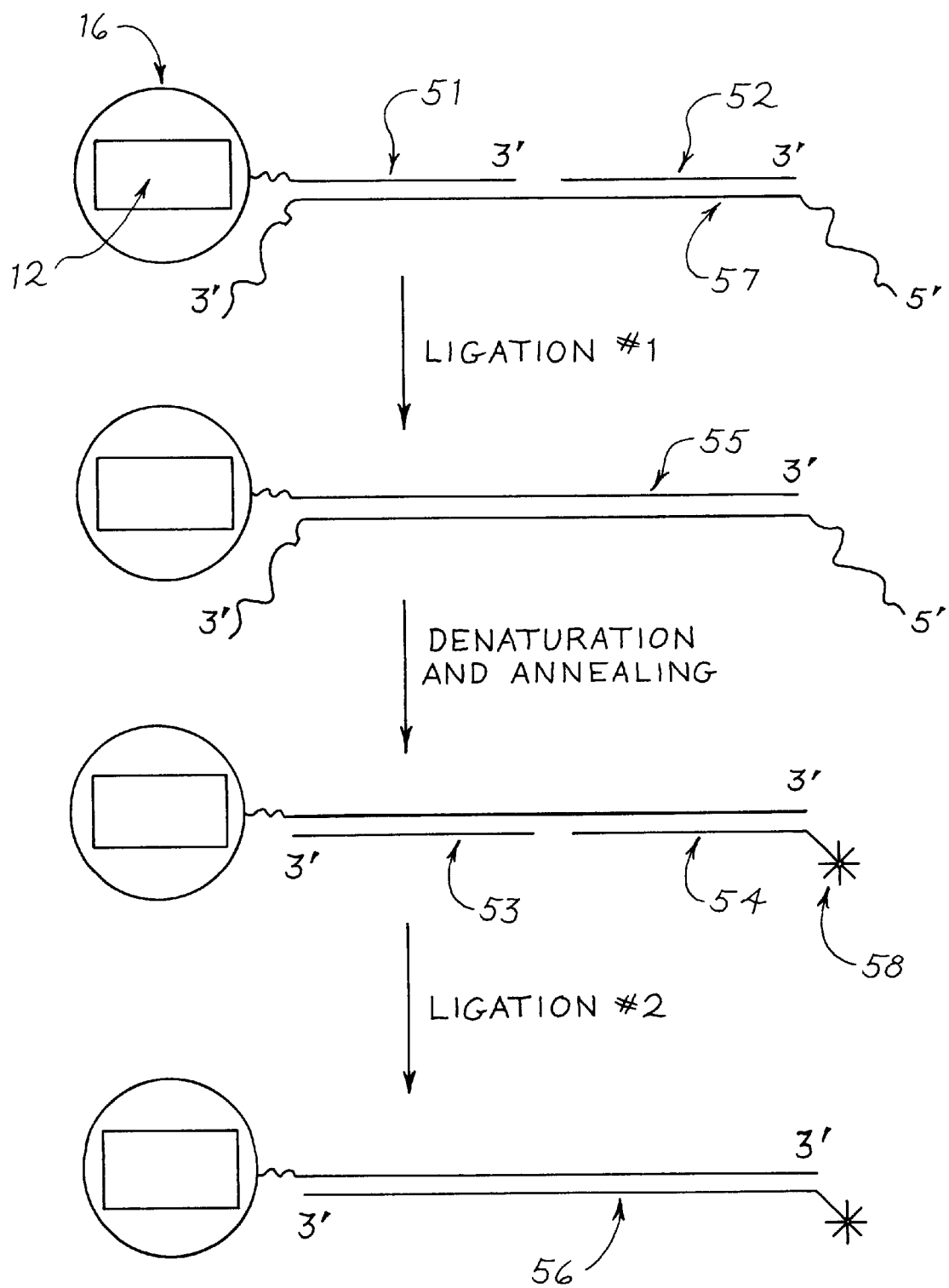
FIG. 13 is a diagram of the amplification of nucleic acids by LCR.

An alternative method for amplification of nucleic acids is the ligase chain ligation (LCR). The scheme for LCR is shown in FIG. 13. The LCR requires four oligonucleotides (51, 52, 53 and 54) and the target DNA 57. Oligonucleotide 51 is attached to the solid phase 16 comprising the transponder 12 through a linker. Oligonucleotides 52 and 53 need to be phosphorylated on the 5' end to enable the ligations. Oligonucleotide 54 carries a fluorophore 58. The target DNA, the four oligonucleotides and thermostable DNA ligase are combined in a single vessel in the ligation buffer. After DNA is denatured by heating, oligonucleotides 51 and 52 undergo the first ligation to form the product, single-stranded DNA 55. After the next denaturation and ligation, the strand 56, complementary to DNA strand 55, is formed. If the amplification process is continued, the amount of the product of LCR increases exponentially in the consecutive cycles of ligation.

A product of a two-step ligation procedure is the double-stranded DNA (55 and 56) attached to the solid phase 16 comprising the transponder 12. This product DNA carries a fluorophore, which allows for the quantitation of the LCR process by measuring the fluorescence of the solid phase particle after the extensive washing is performed. The decoding of the transponder 12 provides the data related to the characteristics of the oligonucleotide 51 (such as its sequence; other data can also be encoded or provided by the transponder). Thus, the two determinations (fluorescence and decoding of the index number) allow for the association of the genetic characteristics, presence or absence of the mutation (as given by the fluorescence) with the region of DNA (as given by the index number).

Figure 14A:
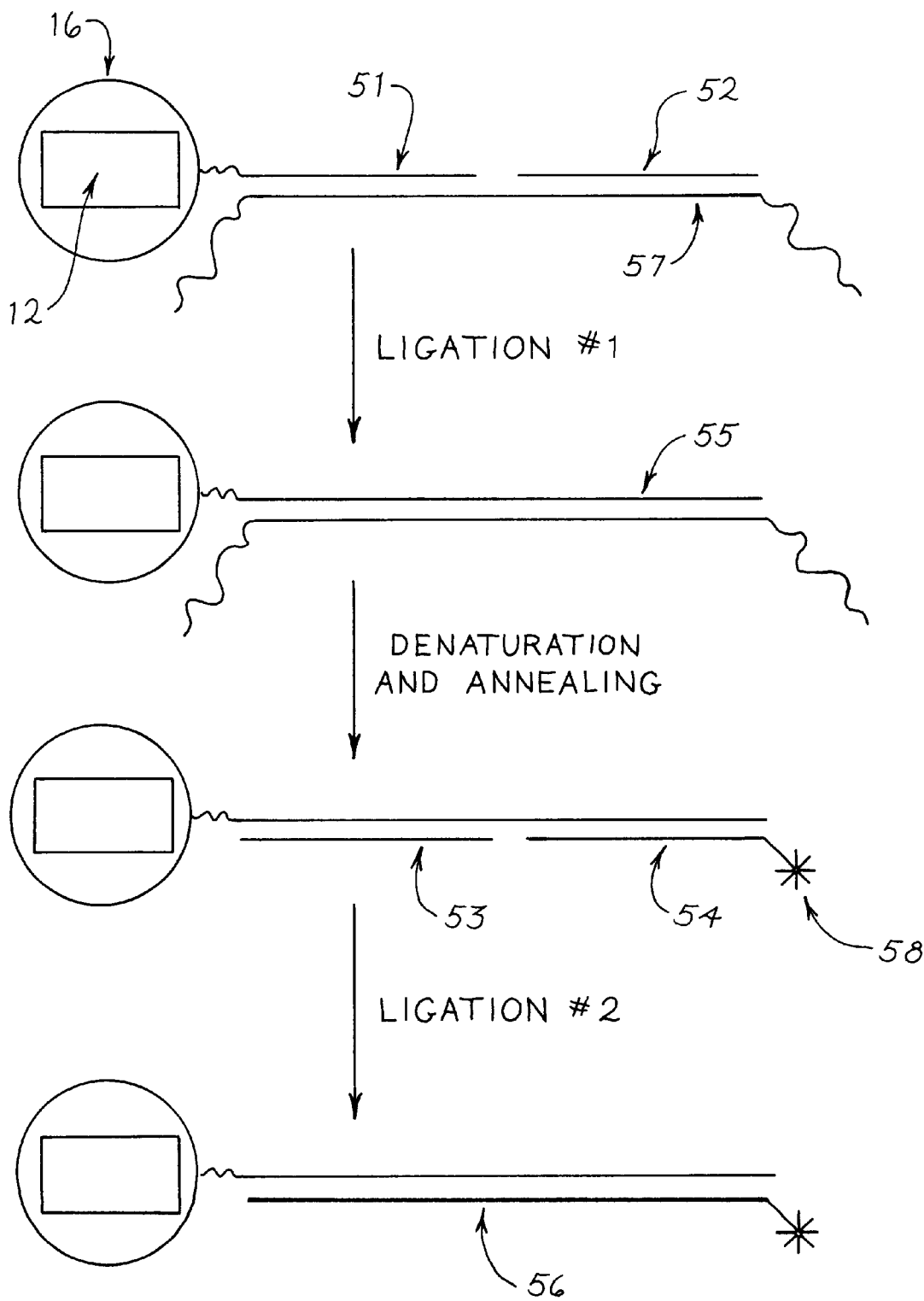
FIG. 14A and FIG. 14B are diagrams of the sandwich immunoassay employing LCR to detect nucleic acids.
Figure 14B:
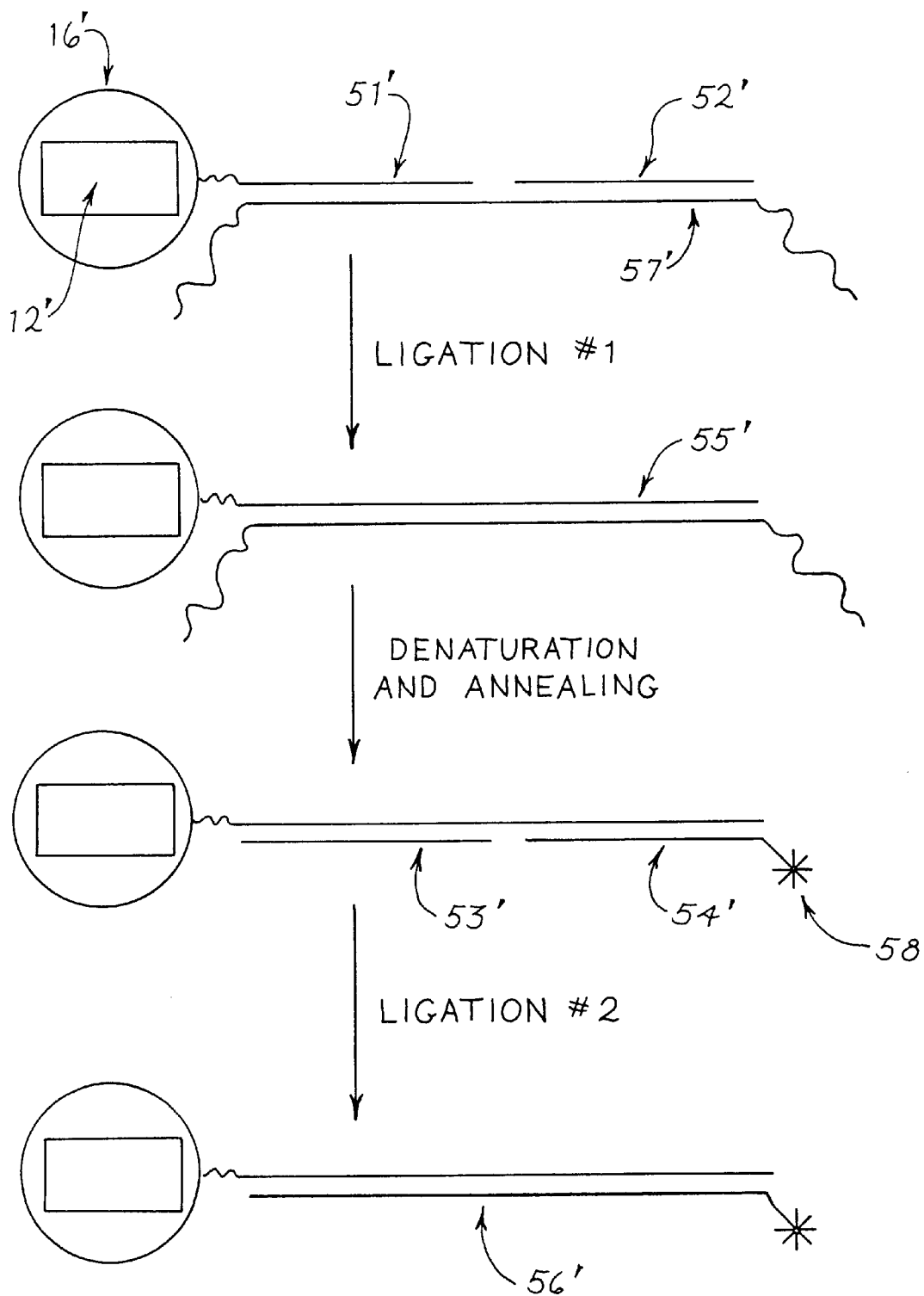

Multiple primers and multiple transponders can be used for more complex genetic analyses by LCR according to this invention. The multiplex LCR assay with two classes of transponders is depicted in FIG. 14A and FIG. 14B. Each class of transponders, 12 and 12', is comprised within two classes of solid phase particles, 16 and 16', and has a unique index number characterizing the class encoded within the transponder. In one implementation of this invention, the index number defines the sequence of the oligonucleotide primer attached to the solid phase particle. The class 16 of solid phase particles is derivatized with oligonucleotide 51, and the class 16'—with oligonucleotide 51'. The ligation partners for 51 and 51', oligonucleotides 52 and 52', are also provided. These oligonucleotides are complementary to the two target DNA molecules, 57 and 57', correspondingly. Two other pairs of oligonucleotides, 53 and 53', as well as 54 and 54' (the latter two derivatized with a fluorophore 58 and complementary to the DNA strands 55 and 55', correspondingly), are implemented in the LCR amplification with the said solid phase particles 16 and 16' and nucleic acid templates 57 and 57'. After the LCR amplification, the solid phase particles are washed and analyzed for fluorescence, and their index number is electronically decoded, and associated with the fluorescence measurement. Thus, the assay provides the information about the genetic characteristics of two different target nucleic acids in the sample.

It is evident to a person skilled in the art that the number of the solid phase particles in the multiplex assay employing LCR can be greater than two, and limited only by the capabilities to manufacture the transponders in quantity, provided that the sufficient care is taken to assure the specificity of the amplification in the single test tube LCR reaction. It is also evident to a person skilled in the art that a single type of the target DNA can be used in the multiplex PCR-based assay (i.e. target DNA 57 is the same as 57'). In such case, the assay provides multiple reads for the multiple genetic determinants in one DNA target. In one particular implementation of the multiplex LCR-based assay on a single target, one type of the oligonucleotide derivatized with a fluorophore 58 can be used (i.e. oligonucleotide 54 can be the same as 54'). In this case, the assay provides the genetic determinants for this part of the target which is downstream (or 3') from the region to which the oligonucleotide 54 anneals.

Figure 15:
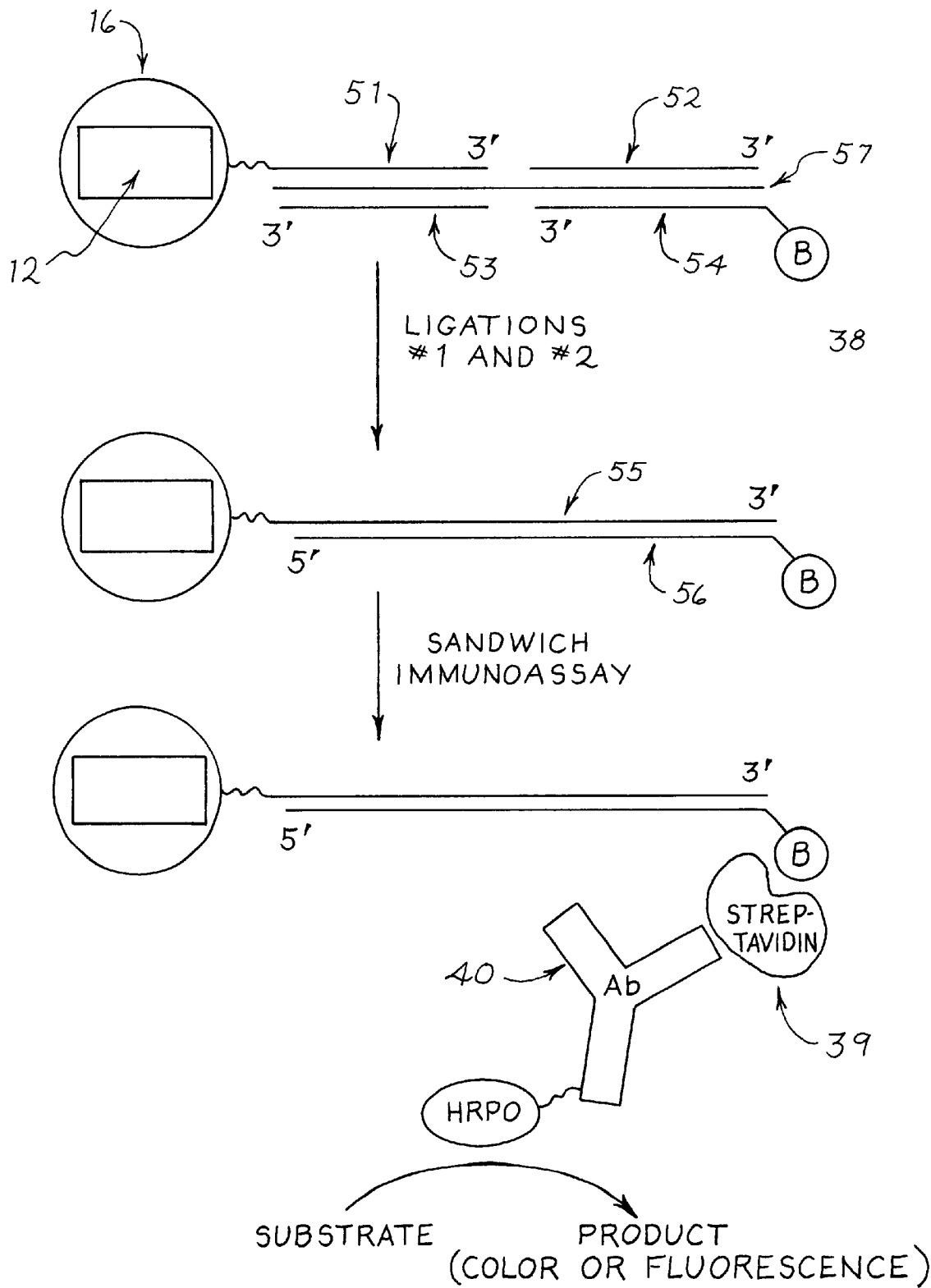
FIG. 15 is a diagram of the sandwich immunoassay employing LCR to detect nucleic acids.

A sandwich assay configuration can also be used to enhance the detection of the product of the solid phase LCR as outlined in FIG. 15. The target DNA 57, oligonucleotides 51 (attached to solid phase 16 comprising the transponder 12), 52, 53 and 54 (conjugated to biotin 38) are implemented in LCR. After the LCR amplification with target 57, the biotinylated product of the reaction, single stranded DNA 56, attached to the solid phase by forming double-stranded DNA complex with the other single-stranded product of LCR 55, is detected in a sandwich assay. The sandwich contains the product double-stranded DNA, biotin, streptavidin 39, anti-streptavidin antibody conjugated to horse radish peroxidase 40 (HRPO). This enzyme catalyses a reaction with a fluorogenic or chromogenic substrate. The amount of the product of the reaction indicates the amount of the DNA amplification product, and the presence or absence of the sequences complementary to oligonucleotides 51, 52, 53 and 54 in the target DNA.

The sandwich is formed by a stepwise addition of reagents. After the PCR amplification, the solid phase is washed to remove unbound primers, reagents and by-products of LCR. Then, streptavidin 39 is added, incubated under conditions to allow it to bind to biotin 38 immobilized on solid support 16, and the solid phase is washed to remove the unbound streptavidin. The anti-streptavidin antibody-HRPO conjugate 40 is then added, incubated under conditions to allow it to bind to streptavidin immobilized on solid support, and the solid phase is washed again to remove the unbound antibody conjugate. The substrate for HRPO is then added to the reaction and incubated for the time sufficient for the enzymatic reaction to take place. The substrate can be either chromogenic, or fluorogenic, or chemiluminescent. The product of the reaction is quantified by measuring the color, fluorescence or chemiluminescence of the reaction.

Figure 16A:
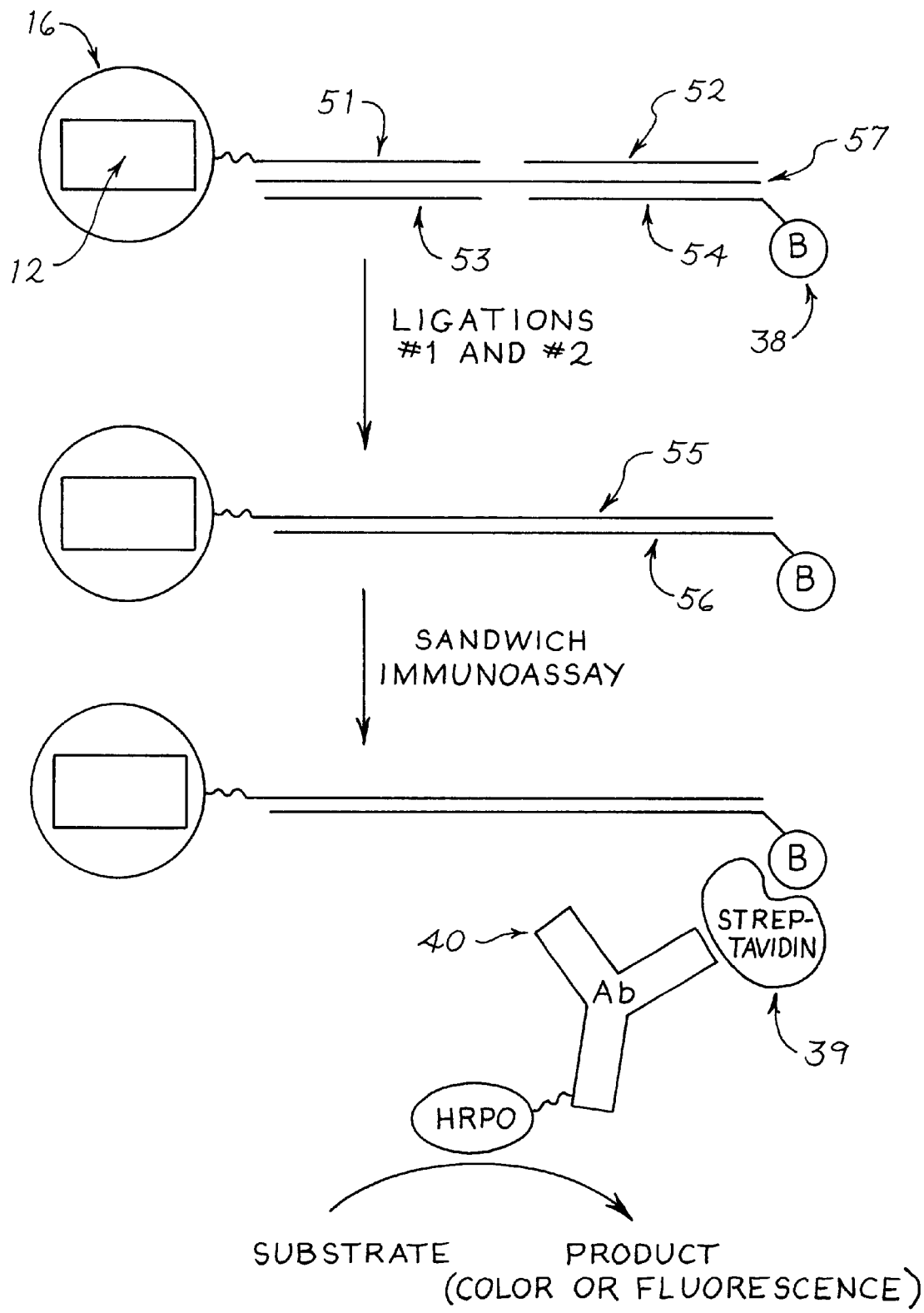
FIG. 16A and FIG. 16B are diagrams of the LCR-based multiplex assay followed by sandwich immunoassay detection.
Figure 16B:
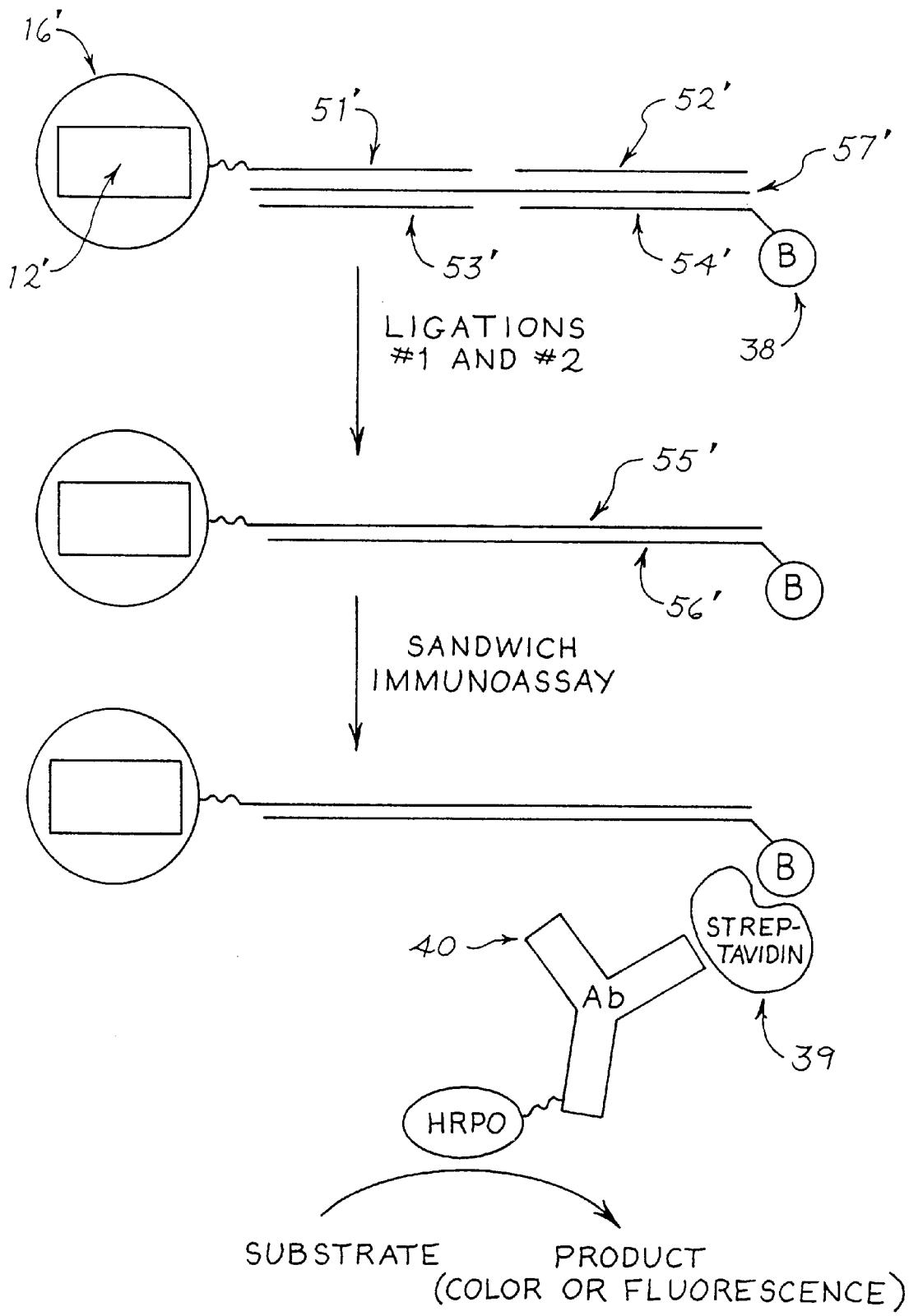

An alternative sandwich detection system for the multiplex LCR assay is presented in FIG. 16A and FIG. 16B for two target DNAs 57 and 57'. In this assay, two sets of four oligonucleotides are used, oligonucleotides 51, 52, 53, 54 and 51', 52', 53', 54'. Oligonucleotides 51 and 51' are attached to the solid phase 16 and 16' which comprises transponders 12 and 12', respectively, and oligonucleotide primers 54 and 54' are conjugated to biotin 38. After the LCR amplification, the reagents for the sandwich assay are added sequentially in the following order: streptavidin 39, wash, anti-streptavidin antibody conjugated to HRPO 40, wash, and the substrate. The color, fluorescence or chemiluminescence of the product is measured and the index number of the transponders is decoded, completing the LCR-based multiplex sandwich assay.

To accelerate the amplification, either by PCR or LCR, the solid phase amplification can be combined with the liquid phase amplification. This is accomplished by adding the soluble form of the oligonucleotide immobilized on the solid phase particles to the reaction. Thus, e.g., the PCR amplification outlined in FIG. 9 would be complemented by the soluble form of oligonucleotide 34, and the amplification involving the oligonucleotide 34 would simultaneously take place on the solid phase 16 and in the liquid. The DNA produced as a result of the liquid phase amplification can be captured by oligonucleotide 34 immobilized on the solid phase 16 or 16' at the completion of the last cycle of PCR, thus contributing to the efficiency of solid phase amplification. In the LCR scheme outlined in FIG. 13, the soluble form of oligonucleotide 51 is used in addition to oligonucleotide 51 bound to solid phase 16 to facilitate the amplification in the liquid phase.

The following are the advantages of the amplification on the solid phase comprising transponders compared with the amplification on large surfaces (e.g. glass):

1. The transponder and the serial number in it provides an immediate identification of the product of the amplification.
2. Preparation of multiple amplification products in a single vessel. The products can be separated after the amplification reaction by decoding the serial number and pooling the transponders having the desired serial numbers corresponding to individual products.
3. The signal, e.g. fluorescence, is detected after a single reaction (PCR or LCR) which is done in one vessel, and not in two or more vessels. The minimum number of steps is usually two, amplification and secondary hybridization to solid phase. In the GeneChip system the number of steps is significantly more than two, involving the amplification, in vitro transcription, fragmentation and annealing to solid phase for detection.
4. The surface area of a transponder compared with a flat plain surface (as in Affymetrix GeneChip system) is larger by a factor of 6 (six sides of a cube, compared with 1 side of a plane. There is a possibility of further increasing the surface area during silicon fabrication of the transponder by applying silicon etching techniques. The amount of PCR or LCR product generated is proportional to the surface area, and it is one of the determinants of the sensitivity of the assay.
5. Small size and mobility of transponders facilitate mixing and annealing of DNA, thus allowing hybridizations involving longer nucleic acid molecules, and accelerating and increasing the specificity of the DNA amplification and detection.
6. Simplified handling. The size of the transponders, a cube preferably having about 0.25 mm on the side, is small enough that the handling of reaction volume (pipeting) is not much different from current handling, thus compatible with many current methods of DNA analysis.

The main application is in nucleic acid based diagnostics to analyze samples of nucleic acids in clinical testing, identity testing, forensic application, veterinary application, agricultural application or for research, and possibly many other areas.

EXAMPLE 1

Multiplex DNA-based Assay on Transponders Employing DNA Synthesized on the Solid Support The glass outer surface of the transponders is first derivatized by an aminoalkylsilane treatment. The transponders (e.g., IPTT-100, BMDS) are cleaned by washing with xylene, followed by a 70% ethanol rinse and air drying. The transponders are then submerged for about 30 seconds in a 2% solution of aminopropyltriethoxysilane (Cat.#A3648, Sigma, St. Louis, Mo.) in dry acetone. The transponders are then sequentially rinsed with dry acetone and distilled water, and then air dried. This procedure is described in the Pierce catalog (pp. T314–T315 of the 1994 catalog, Pierce, Rockford, Ill.).

Nucleic acid probes are then covalently linked to the aminoalkylsilane-treated glass by direct chemical synthesis on the glass support. A thymidine-derivatized support containing a stable nucleoside-urethane linkage is prepared, in which 5'-dimethoxytrityl thymidine is reacted with one equivalent of tolylene-2,6-diisocyanate in the presence of one equivalent of N-ethyldiisopropylamine as a catalyst in pyridine/1,2-dichloroethane to generate the monoisocyanate. The monoisocyanate is not isolated, but is reacted directly with the aminopropyltriethoxysilane-derivatized glass surface of the transponders. The procedure is described in detail in B. S. Sproat and D. M. Brown, A new linkage for solid phase synthesis of oligodeoxyribonucleotides, Nucleic Acids Res. 13, 2979–2987, 1985.

The thymidine-derivatized support containing a stable nucleoside-urethane linkage is used directly for the chemical synthesis of oligodeoxynucleotides by manual synthesis on sintered funnels using standard phosphoramidite-based DNA synthesis reagents, as described in Caruthers, M. H. et al., Deoxyoligonucleotide Synthesis Via The Phosphoramidite Method, Gene Amplification and Analysis, Vol. III (T. S. Papas et al., Eds., Elsevier/North Holland, Amsterdam). The thymidine-urethane linker is resistant to cleavage with base during deprotection, and the resulting product is the deprotected oligonucleotide attached to the glass surface of the transponder through the urethane-thymidilate linker.

The following oligodeoxynucleotide reagents are prepared. Sequence 1 and sequence 2 do not exhibit self-complementarity, are 15 nt long, and are linked to the transponders through a spacer, which is an oligonucleotide having the $(dT)_{10}$ sequence. Oligonucleotides C and D are derivatized at the 5'-end with fluorescein. The sequences are as follows:

transponder-oligonucleotide A: 5'-spacer-sequence1
transponder-oligonucleotide B: 5'-spacer-sequence2
oligonucleotide C: 5'-fluorescein-sequence1complement
oligonucleotide D: 5'-fluorescein-sequence2complement Four assay tubes are prepared and labeled 1, 2, 3 and 4, each assay tube to accommodate two transponders, one transponder carrying oligonucleotide A and the second transponder carrying oligonucleotide B. The transponders are electronically encoded with two alphanumeric characters, namely A1, A2, A3, A4 and B1, B2, B3, B4, where the letter corresponded to the oligonucleotide used to derivatize the transponder, and the digit gave the test tube number into which the given transponder is placed. Thus tube 1 contains transponders A1 and B1; tube 2—A2 and B2; tube 3, A3 and B3; and tube 4, A4 and B4, all immersed in 50 mM Tris-HCl buffer (pH 7.5). Four analytes, X,Y,Z and W, are prepared, as follows. Analyte X contains oligonucleotide C and oligonucleotide D; Y contains oligonucleotide C only, Z contained oligonucleotide D only, and analyte W does not contain any oligonucleotides. The analyte solutions are prepared in 50 mM Tris-HCl (pH 7.5). The concentration of each given oligonucleotide in the analytes X, Y and Z is 10 nM to 10 $\mu$M. After the four tubes are emptied of buffer, but retain the transponders, 2 mls of X,Y,Z and W analyte are added to tubes 1, 2, 3 and 4, respectively. The tubes are heated to 90° C., and slowly cooled to room temperature. Then the transponders are rinsed three times with the buffer. The fluorescence of each transponder is measured on a FluorImager instrument (Molecular Dynamics).

EXAMPLE 2

Multiplex DNA-based Assay on Transponders Employing Conjugation of Oligonucleotides to Solid Support Precleaned transponders (IPTT-100, BMDS) are immersed in a 1% 3-aminopropyltrimethoxysilane solution (Aldrich Chemical, Milwaukee, Wis.) in 95% acetone/water for 2 minutes, washed extensively with acetone (10 washes, 5 minutes each) and dried (110° C. for 45 minutes). The transponders are then treated for 2 hours with 1,4-phenylene diisothiocyanate (Aldrich) (PDC, 0.2% solution in 10% pyridine/dimethyl formamide). The transponders are washed with methanol and acetone and stored at 4° C. in an anhydrous environment. The 5'-amino-modified oligonucleotides to be immobilized on the glass support are dissolved in 100 mM sodium carbonate/bicarbonate buffer (pH 9.0) at a concentration of 2 mM, and a 2 $\mu$l aliquot is applied directly to the PDC-derivatized transponders and incubated at 37° C. in a closed vessel for 2 hours. The transponders are then washed with NH$_4$OH, three times with water and air dried at room temperature. This derivatization procedure is based on a protocol described in Guo et al. (Direct Fluorescence Analysis Of Genetic Polymorphism By Hybridization With Oligonucleotide Arrays On Glass Support. Nucleic Acids Res. 22, 5456–5465, 1994).

The following oligodeoxynucleotide reagents are prepared. Sequence1 and sequence 2 are 15 nt long, and are linked to the transponders through an oligonucleotide spacer having the $(dT)_{10}$ sequence. Oligonucleotides C and D are derivatized at the 5'-end with fluorescein. The sequences are as follows:

transponder-oligonucleotide A: 5'-spacer-sequence1
transponder-oligonucleotide B: 5'-spacer-sequence2
oligonucleotide C: 5'-fluorescein-sequence1complement
oligonucleotide D: 5'-fluorescein-sequence2complement Four assay tubes are prepared and labeled 1, 2, 3 and 4, each tube to accommodate two transponders, one transponder carrying oligonucleotide A and the second transponder carrying oligonucleotide B. The transponders are electronically encoded with two alphanumeric characters, namely A1, A2, A3, A4 and B1, B2, B3, B4, where the letter corresponded to the oligonucleotide used to derivatize the transponder, and the digit gave the test tube number into which the given transponder is placed. Thus tube 1 contains transponders A1 and B1; tube 2—A2 and B2; tube 3, A3 and B3; and tube 4, A4 and B4, all immersed in 50 mM Tris-HCl buffer (pH 7.5). Four analytes, X,Y,Z and W, are prepared, as follows. Analyte X contains oligonucleotide C and oligonucleotide D; Y contains oligonucleotide C only, Z contained oligonucleotide D only, and analyte W does not contain any oligonucleotides. The buffer is 50 mM Tris-HCl (pH 7.5). The concentration of each given oligonucleotide in the analytes X, Y and Z is 10 $\mu$M. After the four tubes are emptied of buffer, but retain the transponders, 2 mls of X,Y,Z and W analyte are added to tube 1,2,3 and 4, respectively. The tubes are heated to 90° C., and slowly cooled to room temperature. Then the transponders are rinsed three times with the buffer. The fluorescence of each transponder is measured on a Fluorimager (Molecular Dynamics).

EXAMPLE 3

Conjugation Of Streptavidin To the Glass Surface of Transponders

The outside glass surface of transponders (IPTT-100, BMDS) is derivatized through the aminoalkylsilane treatment outlined above, and a linker is attached to the aminoalkylsilane-treated glass. A variety of methods can be used, as reviewed in Enzyme Immunodiagnostics, E. Kurstak, Academic Press, New York, 1986, pp. 13–22. This procedure a homobifunctional NHS-ester cross-linker, $BS^3$, bis(sulfosuccinimidyl)suberate (Pierce Cat.# 21579, described on p. T159 of the 1994 Pierce catalog).

The transponders are immersed in the 10 mM solution of $BS^3$ in 100 $\mu$M phosphate buffer (pH 7.0–7.4) for 5 to 60 minutes at room temperature, and the transponders are rinsed with water. A 10–100 $\mu$M streptavidin solution in 100 mM phosphate buffer (pH 7.4–8.0) is prepared. The transponders are submerged in the streptavidin solution and incubated at room temperature for 2–3 hours. The transponders are rinsed three times with 100 mM phosphate buffer (pH 7.4–8.0). The unreacted sites on the glass are blocked by incubating in Blocker BLOTTO in PBS (phosphate-buffered saline) (Pierce, Cat.# 37526) for 2 hrs. The transponders are rinsed three times with 100 mM phosphate buffer (pH 7.4–8.0), and stored in this buffer at 4° C.

EXAMPLE 4

Detection of a Point Mutation in the N-ras Gene

Point mutations in the N-ras gene are frequently observed in various hematological and solid tumors. A wellcharacterized mutation is a G→C mutation in the first position of the 12th codon of the N-ras gene. The present example provides a method to detect this mutation implementing transponders.

The sequence of the first exon of the N-ras gene is given in Table 1(SEQ ID NO. 1–2). The glass surface of transponders (IPTT-100, BMDS) used in this example is derivatized with streptavidin using the conjugation method described in Example 3. The following oligodeoxynucleotides are chemically synthesized:
(1) GACTGAGTACAAACTGGTGG, (SEQ ID NO:3) corresponding to residues 3–22 of exon 1;
(2) CTCTATGGTGGGATCATATT-biotin, (SEQ ID NO:4) corresponding to residues 111–91;
(3) AACTGGTGGTGGTTGGAGCA, (SEQ ID NO:5) corresponding to residues 14–33, Oligonucleotide (2) is biotinylated at the 5' end. These sequences were previously used to perform mini-sequencing using scintillating microplates by Ihalainen et al. (BioTechniques, 16, 938–943, 1994). Cellular DNA from patient samples is purified using the standard Blin and Safford procedure (Sambrook et al., 1989, Molecular Cloning: A Laboratory Manual, 2nd Edition, Cold Spring Harbor Laboratory Press, Cold Spring Harbor, N.Y.). PCR amplification of DNA using primers (1) and (2) is done on the Perkin-Elmer Cycler 9600, employing 50 cycles of amplification. Each cycle involved a 1 minute denaturation at 94° C., 1 minute annealing at 55° C. and 1 minute chain extension at 72° C. in a final volume of 100 µl. The single DNA strand carrying biotin is captured on two transponders conjugated to streptavidin by incubating the product of the PCR reaction with the transponders in a buffer containing 150 mM NaCl, 20 mM sodium phosphate (pH 7.4) and 0.1% Tween-20 at 37° C. with gentle shaking for 90 minutes. The bound PCR product was denatured with 50 mM NaOH for 5 minutes at room temperature. The transponders are then washed extensively 3–5 times with a buffer (40 mM Tris-HCl, pH 8.8, 1 mM EDTA, 50 mM NaCl, 0.1% Tween-20). The patient name, consisting of six alphanumeric characters, is encoded on the two transponders using a dedicated read-write scanner.

The diagnostic chain extension reaction is configured for one transponder as follows. The primer, oligonucleotide (3) is at a final concentration of 0.4 M, $^3$H dCTP or $^3$H dGTP (Amersham) at 0.2 µM, and 4 units of Taq polymerase, in a final volume of 1 ml of a buffer containing 50 mM KCl, 10 mM Tris-HCl (pH 9.0 at 25° C.), 0.1% Triton X-100, 4 mM MgCl. The final volume and the test tube type are adjusted depending on the number of transponders so that the whole surface of the transponders is covered with buffer. The reaction is incubated at 55° C. for 10 minutes with gentle shaking.

To determine whether the mutation is present, transponders are used in two DNA chain extension reactions. The first reaction contains $^3$H dCTP and no other dNTPs, the second one contains $^3$H dGTP and no other dNTPs. Since the transponders are individually encoded with the patient's name, several transponders can be placed in the vessel where the reaction takes place.

After the reactions are completed, the transponders are washed 3 times as described above, and dried for 60 minutes at room temperature. The transponders are subjected to the electronic decoding, which is followed by counting of the radioactivity associated with the transponders in a scintillation counter, with or without scintillation fluid. Radioactivity associated with the reaction employing $^3$H dCTP indicates the presence of the mutation in the sample DNA.

TABLE 1

Sequence of exon 1 of the N-ras gene (SEQ ID NOs: 1–2)

```
                                  *
AT GACTGAGTACA AACTGGTGGTGGTTGGAGCA GGTGGTGTTGGGAAAAG         50
TACTGACTCATGTTTGACCACCACCAACCTCGTCCACCACAACCCTTTTC
MetThrGluTyrLysLeuValValValGlyAlaGlyGlyValGlyLysSe

29
CGCACTGACAATCCAGCTAATCCAGAACCACTTTGTAGATGAATATGATC           100
GCGTGACTGTTAGGTCGATTAGGTCTTGGTGAAACATCTAC TTATACTAG
rAlaLeuThrIleGlnLeuIleGlnAsnHisPheValAspGluTyrAspP

CCACCATAGAG gtgaggccc                                        120
GGTGGTATCTC cactccggg
roThrIleGlu
```

Legend to Table 1:
Bold: Oligonucleotides (1) and (2);
Underlined: oligonucleotide primer (3);
Asterisk – indicates the position of the mutation G-→C at codon 12. The sequence is from GenBank 86, entry HNSRAS1.

EXAMPLE 5

Assay for a Mutant N-ras Gene by Solid Phase PCR on Transponder

The present example provides a procedure to detect a G→C mutation in the first position of the 12th codon of the human N-ras gene implementing the solid phase PCR amplification of DNA on transponders.

The sequence of the first exon of the N-ras gene and of three PCR primers is given in Table 2. The sequences of primers 1 and 2 differ at one nucleotide residue at their 3' ends. Primer 1 has the C residue that occurs in the mutant allele of the exon, and primer 2 has the G residue that occurs in the wild-type allele of the exon. Thus, the PCR amplification with primer 1 is enabled only on the mutant allele, and the amplification with primer 2 is enabled only on the wild-type allele.

The glass surface of transponders (IPTT-100, BMDS) used in this example is derivatized with the oligonucleotide primers 1 and 2 employing the method described in Example 2 on the transponders of two classes, one class encoded with alphanumeric character "1" (index number) and derivatized with primer 1, the other class encoded with alphanumeric character "2" and derivatized with primer 2. Primer 3 is derivatized with fluorescein on the 5' end. Small amount of the template DNA, i.e. exon 1 as shown in Table 2, the two types of transponders and primer 3 at 1 μM concentration are added to a single vessel in the standard PCR buffer. The mixture is heated to 95° C., and the thermostable polymerase is added to the vessel. The PCR amplification is performed for the number of cycles commensurate with the amount of the template DNA (typically 5–50 cycles). The temperature shifts within one cycle are given in Example 4. After the PCR amplification is completed, the transponders are thoroughly washed, their surface fluorescence is measured, and the index number ("1" or "12") is decoded electronically on a scanner. A high fluorescence reading on transponder class 1, and a low reading on the class 2 transponder indicates that the wild-type N-ras allele was the template DNA. A low fluorescence reading on transponder class 1, and a high reading on the class 2 transponder indicates that the mutant N-ras allele was the template DNA.

TABLE 2

Sequence of exon 1 of the N-ras gene (SEQ ID NOS: 1-2) and primers for solid phase (SEQ ID NOS: 6, 7 and 9)

PCR

```
                                     3'
Primer 1: SP-AACTGGTGGTGGTTGGAGCAC (SEQ ID NO:6)

Primer 2: SP-AACTGGTGGTGGTTGGAGCAG (SEQ ID NO:7)
ATGACTGAGTACAAACTGGTGGTGGTTGGAGCAG GTGGTGTTGGGAAAAG           50
TACTGACTCATGTTTGACCACCACCAACCTCGTCCACCACAACCCTTTTC
MetThrGluTyrLysLeuValValValGlyAlaGlyGlyValGlyLysSe 31
CGCACTGACAATCCAGCTAATCCAGAACCACTTTGTAGATGAATATGATC           100
GCGTGACTGTTAGGTCGATTAGGTCTTGGTGAAACATCTACTTATACTAG
rAlaLeuThrIleGlnLeuIleGlnAsnHisPheValAspGluTyrAspP Primer 3: 3'-TTATACTAGGGTGGTATCTC-F (SEQ ID NO:10)
CCACCATAGAGgtgaggccc                                         120
GGTGGTATCTCcactccggg
roThrIleGlu
```

Legend: The PCR primers are highlighted in bold. The first nucleotide at codon 12 is highlighted in bold. 3' and 5' ends of oligonucleotide primers are indicated. F, fluorophore at the 5' end of primer 3. SP, solid phase particle comprising a transponder.

0

EXAMPLE 6

Assay for a Mutant N-ras Gene by PCR Done Both in Solution and on Solid Phase

The objective of this experiment is to increase the efficiency of PCR while maintaining the convenience of a single test tube assay. The experiment is done as in Example 4, with an exception for allowing soluble forms of primers 1 and 2 (as in Table 2) at a final concentration of 0.1 to 1 μM in addition to the transponder-conjugated primers in the assay.

After the PCR amplification is completed, the transponders are thoroughly washed, their surface fluorescence is measured, and the index number ("1" or "2") is decoded electronically on a scanner. A high fluorescence reading on transponder class 1, and a low reading on the class 2 transponder indicates that the wild-type N-ras allele was the template DNA. A low fluorescence reading on transponder class 1, and a high reading on the class 2 transponder indicates that the mutant N-ras allele was the template DNA.

EXAMPLE 7

Assay for a Mutant N-ras Gene by PCR in a Sandwich Format

The objective of this experiment is to assure the sensitivity of the detection of the PCR products while using the industry standard sandwich assay format.

The experiment is done as in Example 4, except that primer 3 is derivatized with biotin on its 5' end (and not with fluorescein). The derivatization is done during the chemical synthesis of the oligonucleotide using methods well known in the art.

After the PCR amplification is completed, the transponders are thoroughly washed, immersed in a solution of the conjugate of streptavidin to calf intestinal alkaline phosphatase (0.1–10 μg/ml), incubated at room temperature for 1 hour to allow the conjugate to bind to biotin immobilized on the transponders, and thouroghly washed again. A 0.1% solution of attophos, a precipitating fluorogenic substrate for alkaline phosphatase (JBL Scientific, San Luis Obispo, Calif.) is added to the vessel carrying the transponders. The vessel is incubated at room temperature for 2 to 30 min, depending on the desired sensitivity of the assay, after which the transponders are washed to remove excess substrate and that fraction of the product of the enzymatic reaction which did not precipitate. Subsequenty, the fluorescence of the transponders' surfaces is measured, and the index number ("1" or "2") is decoded electronically on a scanner. A high fluorescence reading on transponder class 1, and a low reading on the class 2 transponder indicates that the wild-type N-ras allele was the template DNA. A low fluorescence reading on transponder class 1, and a high reading on the class 2 transponder indicates that the mutant N-ras allele was the template DNA.

EXAMPLE 8

Assay for a Mutant N-ras Gene by LCR

The present example provides a procedure to detect a G→C mutation in the first position of the 12th codon of the human N-ras gene implementing the solid phase LCR amplification of DNA on transponders.

The sequences of residues 1–66 of the first exon of the N-ras gene and of LCR primers is given in Table 3. A variation of LCR implemented here is also known in the art as PLCR, and it involves the primers designed with a gap of 2—3 nt between the LCR primers. The discrimination between the wild-type and mutant allele is due to the choice of nucleotide residue at the 3' ends of primers 2A and 2B, and at the 3' end of primers 3A and 3B. Primers 2A and 3A are specific for the wild-type allele, and primers 2B and 3B are specific for the mutant allele. The first step of LCR involves the chain extension with a thermostable DNA polymerase to fill the gap between the LCR primers, in the second step, the primers that annealed to the same template are ligated by a thermostable ligase.

The glass surface of transponders (IPTT-100, BMDS) used in this example is derivatized with the oligonucleotide primers 3A and 3B employing the method described in Example 2 on the transponders of two classes, one class encoded with alphanumeric character "A" (index number) and derivatized with primer 3A, the other class encoded with alphanumeric character "B" and derivatized with primer 3B. Primers 2A and 2B are derivatized with fluorescein on the 5' end. The following constituents are placed into one vessel:
(a) a small amount of the target DNA, i.e. a DNA fragment from exon 1 of the N-ras gene as shown in Table 3;
(b) the two types of transponders derivatized with primers 3A and 3B;
(c) primers 1, 2A, 2B and 4 at 2 nM concentration;
(d) LCR buffer, final composition having 80 mM KOH/KCl, 50 mM EPPS, 1 mM MgCl$_2$, 10 mM NH$_4$Cl, 1 mM DTT, 10 μg/ml BSA and 1 mM NAD,
(e) four nucleotides (dATP, dCTP, dGTP and TTP at 1 μM concentration;
(f) 0.5–5 nick closing units of Thermus aquaticus DNA ligase per 1 μl of buffer;
(g) 0.03–0.2 units of the Taq polymerase Stoffel fragment per 1 μl of buffer.

First, the vessel is incubated at 97° C. for 3 min to denature the nucleic acids present. Then the vessel is subjected to 20–60 cycles (depending on the amount of target DNA) of temperature changes, each cycle involving a 94° C. incubation for 1 min and a 65° C. incubation for 4 min.

After the solid phase LCR amplification is completed, the transponders are thoroughly washed, their surface fluorescence is measured, and the index number ("A" or "B") is decoded electronically on a scanner. A high fluorescence reading on transponder class A, and a low reading on the class B transponder indicates that the wild-type N-ras allele was the target DNA. A low fluorescence reading on transponder class A, and a high reading on the class B transponder indicates that the mutant N-ras allele was the target DNA.

TABLE 3

Scheme of LCR on transponders

```
SCHEME FOR THE TOP STRAND OF THE TARGET DNA (SEQ ID NO:8):
5'                                            *                              3'
ATGACTGAGTACAAACTGGTGGTGGTTGGAGCAGGTGGTGTTGGGAAAAGCGCACTGACAATCCAG
           TTTGTTTGACCACCACCAACCTC  CCACCACAACCCTTTTCGCGAA-F
           3'       Primer 1          Primer 2A     5'
                                     GCACCACAACCCTTTTCGCGAA-F
                                          Primer 2B (SEQ ID NO:12)

SCHEME FOR THE BOTTOM STRAND OF THE TARGET DNA (SEQ ID NO:19):
                     Primer 3B (SEQ ID NO:13)
           SP1-AAACTGGTGGTGGTTGGAGCAC
               5'     Primer 3A (SEQ ID NO:14) Primer 4 (SEQ ID NO:15) 3'
           SP2-AAACTGGTGGTGGTTGGAGCAG    GTGTTGGGAAAAGCGCACTGACCC
TACTGACTCATGTTTGACCACCACCAACCTCGTCCACCACAACCCTTTTCGCGTGACTGTTAGGTC
3'                                            *
MetThrGluTyrLysLeuValValValGlyAlaGlyGlyValGlyLysSerAlaLeuThrIleGln PRODUCTS OF LCR:
Product A (using primers 1, 2A, 3A and 4):                    5'
    SP1-TTTTTTGACCACCACCAACCTCGTCCACCACAACCCTTTTCGCGTGACAA (SEQ ID NO:16)
          AAAACTGGTGGTGGTTGGAGCAGGTGGTGTTGGGAAAAGCGCACTGACCC-F (SEQ ID NO:20)

Product B (using primers 1, 2B, 3B and 4):                    5'
    SP2-TTTTTTGACCACCACCAACCTCGTGCACCACAACCCTTTTCGCGTGACAA (SEQ ID NO:17)
          AAAACTGGTGGTGGTTGGAGCACGTGGTGTTGGGAAAAGCGCACTGACCC-F (SEQ ID NO:18)
```

Legend to Table 3:
SP1: Solid phase comprising transponder encoded with the index number A;
SP2: Solid phase comprising transponder encoded with the index number B;
F: Fluorophore;
5', 3': Denote the polarity of single-stranded DNA;
Asterisk: Indicates the position of the G/C -→ C/G mutation at codon 12;
Underline: Indicates the position of the discriminating residues in primers 2A, 2B, 3A, and 3B;
Bold: Mismatched residues at the ends of the LCR primer to facilitate LCR, or highlighting of the solid phase or fluorophore;
Amino acid sequence of the relevant part of exon 1 of the N-ras gene is shown at the bottom of the table;
Product A: Double-stranded DNA made if the target is the wild-type N-ras gene (strand polarity is indicated);
Product B: Double-stranded DNA made if the target is the mutant N-ras gene (strand polarity is indicated).

I claim:

1. A method of detecting a target nucleic acid sequence in a sample, comprising the steps of:
    (a) providing a solid phase comprising particles having transponders, the transponders having memory elements, the particles having a nucleic acid probe attached to a surface of the solid phase particles, the probe having a sequence complementary to a target sequence, the transponders having an index number encoded in the memory element;
    (b) contacting the solid phase with a sample to form a sample mixture;
    (c) increasing the amount of the target nucleic acid subjected to analysis by PCR amplification, using at least one oligonucleotide primer which is not immobilized on the solid phase, said PCR amplification comprising at least one cycle of:
        (1) denaturation of nucleic acids in the sample mixture;
        (2) hybridization of nucleic acids in the sample mixture;
        (3) chain extension with DNA polymerase;
    (d) analyzing the solid phase to detect the presence of a label indicative of binding of the target nucleic acid; and
    (e) decoding the data encoded on transponders using the dedicated read/write scanner to identify the class of transponders to which analytes are bound.

2. The method of claim 1, wherein the sample mixture further comprises a soluble nucleic acid probe the sequence of which is substantially the same as the sequence of the probe attached to a surface of the solid phase particle.

3. A method of performing a multiplex solid phase assay for target nucleic acids in a sample, comprising the steps of:
    (a) providing a particulate solid phase, the particles of the solid phase having transponders, the transponders having memory elements, and an oligonucleotide probe attached to a surface of the particle, the oligonucleotide probe complementary to a target sequence; p1 (b) the transponders comprising two or more classes of encoded transponders, each class having a different oligonucleotide bound to the surface of the particle, and each class having a different index number encoded on the transponders memory elements;
    (c) contacting the solid phase with a sample to form a sample mixture, the sample mixture containing two more transponders of different classes;
    (d) increasing the amount of the target nucleic acid subjected to analysis by PCR amplification, using at least one oligonucleotide primer which is not immobilized on the solid phase, said PCR amplification comprising at least one cycle of:
        (1) denaturation of nucleic acids in the sample mixture;
        (2) hybridization of nucleic acids in the sample mixture;
        (3) chain extension with DNA polymerase;
    (e) removing unbound sample components from the sample mixture;
    (f) analyzing the solid phase to detect a label indicative of the presence of bound analytes; and
    (g) decoding the data encoded on the transponders to identify the class of transponder to which an analyte is bound.

4. A method of detecting target nucleic acids in a sample, comprising the steps of:
   (a) introducing into the sample at least two populations of solid phase particles, each particle having a transponder and having an oligonucleotide probe attached to its surface, a first population having an oligonucleotide probe that hybridizes to a different target nucleic acid than a second population and the transponders in the first population being encoded with a different identification than the transponders of the second population;
   (b) increasing the amount of the target nucleic acid subjected to analysis by PCR amplification, using at least one oligonucleotide primer which is not immobilized on the solid phase, said PCR amplification comprising at least one cycle of:
      (1) denaturation of nucleic acids in the sample mixture;
      (2) hybridization of nucleic acids in the sample mixture;
      (3) chain extension with DNA polymerase;
   (c) analyzing the particles to detect a label indicating that target nucleic acid has bound to the probe; and
   (d) decoding the transponder to identify the probe.

5. The method of claim 1 wherein at least one oligonucleotide primer which is not immobilized on the solid phase carries a label which is the binding partner for another biomolecule, and wherein the analyzing of the solid phase for the binding of the target nucleic acid comprises:
   (a) adding the said biomolecule to the sample mixture;
   (b) a detection step specific for the biomolecule.

6. A method of detecting a target nucleic acid sequence in a sample, comprising the steps of:
   (a) providing a solid phase comprising particles having transponders, the transponders having memory elements, the particles having a nucleic acid probe attached to a surface of the solid phase particles, the probe having a sequence complementary to a target sequence, the transponders having an index number encoded in the memory element;
   (b) contacting the solid phase with a sample to form a sample mixture;
   (c) performing at least one cycle of the ligation reaction, said ligation involving at least one oligonucleotide primer which is not immobilized on the solid phase, said ligation cycle comprising the following steps:
      (1) denaturation of nucleic acids in the sample mixture;
      (2) hybridization of nucleic acids in the sample mixture;
      (3) enzymatic reaction with a DNA ligase;
   (d) analyzing the solid phase to detect the presence of a label indicative of binding of the target nucleic acid; and
   (e) decoding the data encoded on transponders using the dedicated read/write scanner to identify the class of transponders to which analytes are bound.

7. The method of claim 6, wherein the said sample mixture further comprises a soluble nucleic acid probe the sequence of which is substantially the same as the sequence of the probe attached to a surface of the solid phase particle.

8. A method of performing a multiplex solid phase assay for target nucleic acids in a sample, comprising the steps of:
   (a) providing a particulate solid phase, the particles of the solid phase having transponders, the transponders having memory elements, and an oligonucleotide probe attached to a surface of the particle, the oligonucleotide probe complementary to a target sequence;
   (b) the transponders comprising two or more classes of encoded transponders, each class having a different oligonucleotide bound to the surface of the particle, and each class having a different index number encoded on the transponders memory elements;
   (c) contacting the solid phase with a sample to form a sample mixture, the sample mixture containing two more transponders of different classes;
   (d) performing at least one cycle of the ligation reaction, said ligation involving at least one oligonucleotide primer which is not immobilized on the solid phase, said ligation cycle comprising the following steps:
      (1) denaturation of nucleic acids in the sample mixture;
      (2) hybridization of nucleic acids in the sample mixture;
      (3) enzymatic reaction with a DNA ligase;
   (e) removing unbound sample components from the sample mixture;
   (f) analyzing the solid phase to detect a label indicative of the presence of bound analytes; and
   (g) decoding the data encoded on the transponders to identify the class of transponder to which an analyte is bound.

9. A method of detecting target nucleic acids in a sample, comprising the steps of:
   (a) introducing into the sample at least two populations of solid phase particles, each particle having a transponder and having an oligonucleotide probe attached to its surface, a first population having an oligonucleotide probe that hybridizes to a different target nucleic acid than a second population and the transponders in the first population being encoded with a different identification than the transponders of the second population;
   (b) performing at least one cycle of the ligation reaction, said ligation involving at least one oligonucleotide primer which is not immobilized on the solid phase, said ligation cycle comprising the following steps:
      (1) denaturation of nucleic acids in the sample mixture;
      (2) hybridization of nucleic acids in the sample mixture;
      (3) enzymatic reaction with a DNA ligase;
   (c) analyzing the particles to detect a label indicating that target nucleic acid has bound to the probe; and
   (d) decoding the transponder to identify the probe.

10. The method of claim 6 wherein at least one oligonucleotide primer which is not immobilized on the solid phase carries a label which is the binding partner for another biomolecule, and wherein the analyzing of the solid phase for the binding of the target nucleic acid comprises:
    (a) adding the said biomolecule to the sample mixture;
    (b) a detection step specific for the biomolecule.

11. The method of claim 6 wherein the ligation cycle further comprises an extension of the oligonucleotide primer with DNA polymerase.

12. The method of claim 7 wherein the ligation cycle further comprises an extension of the oligonucleotide primer with DNA polymerase.

13. The method of claim 8 wherein the ligation cycle further comprises an extension of the oligonucleotide primer with DNA polymerase.

14. The method of claim 9 wherein the ligation cycle further comprises an extension of the oligonucleotide primer with DNA polymerase.

15. The method of claim 10 wherein the ligation cycle further comprises an extension of the oligonucleotide primer with DNA polymerase.

16. A kit for detecting the presence of a nucleic acid in a sample, comprising:
   (a) at least one assay vessel, containing at least one solid phase particle having a transponder, and an oligonucleotide probe bound to a surface of the particle; and
   (b) at least one label reagent.

17. The kit of claim 16, further comprising a thermostable DNA polymerase and deoxynucleotide triphosphates for PCR amplification.

18. The kit of claim 16 further comprising a thermostable DNA ligase.

19. The kit of claim 18, further comprising a thermostable DNA polymerase.

* * * * *

UNITED STATES PATENT AND TRADEMARK OFFICE
CERTIFICATE OF CORRECTION

PATENT NO. : 6,051,377
DATED : April 18, 2000
INVENTOR(S) : Wlodek Mandecki

It is certified that error appears in the above-identified patent and that said Letters Patent is hereby corrected as shown below:

<u>Title page,</u>
<u>Column 1,</u>
Line 29, de 1 blete "Mroczkowski et al." and substitute -- Biegel -- in its place.
After line 29, insert the following: -- 5,284,748  2/1994  Mroczkowski et al. --.

<u>Claim 3,</u>
Line 7, delete "pl", and "(b)" should be a new indented paragraph.

<u>Claim 8,</u>
Line 12, delete "transponders" and substitute -- transponders' -- in its place.

Signed and Sealed this

Thirtieth Day of October, 2001

Attest:

NICHOLAS P. GODICI
*Attesting Officer*   *Acting Director of the United States Patent and Trademark Office*